United States Patent
Zalipsky et al.

(10) Patent No.: US 7,303,760 B2
(45) Date of Patent: *Dec. 4, 2007

(54) METHOD FOR TREATING MULTI-DRUG RESISTANT TUMORS

(75) Inventors: Samuel Zalipsky, Redwood City, CA (US); Alberto Gabizon, Jerusalem (IL)

(73) Assignees: Alza Corporation, Mountain View, CA (US); Yissum Research Development Company of the Hebrew University of Jerusalem, Jerusalem (IL)

( * ) Notice: Subject to any disclaimer, the term of this patent is extended or adjusted under 35 U.S.C. 154(b) by 789 days.

This patent is subject to a terminal disclaimer.

(21) Appl. No.: 10/714,085

(22) Filed: Nov. 14, 2003

(65) Prior Publication Data

US 2004/0161455 A1    Aug. 19, 2004

Related U.S. Application Data

(63) Continuation-in-part of application No. 10/057,839, filed on Jan. 25, 2002, now Pat. No. 6,984,396, which is a continuation of application No. 09/556,610, filed on Apr. 21, 2000, now Pat. No. 6,365,179.

(60) Provisional application No. 60/467,070, filed on Apr. 30, 2003, provisional application No. 60/130,897, filed on Apr. 23, 1999.

(51) Int. Cl.
*A61K 9/127* (2006.01)
*C07F 9/02* (2006.01)
*C07F 53/00* (2006.01)
*C07F 321/00* (2006.01)

(52) U.S. Cl. ............ 424/450; 514/506; 514/767; 514/768; 554/78; 554/80; 554/81; 554/85; 564/541

(58) Field of Classification Search ............ None
See application file for complete search history.

(56) References Cited

U.S. PATENT DOCUMENTS 4,021,449 A    5/1977   Fujimoto et al.

(Continued)

FOREIGN PATENT DOCUMENTS

EP    0 317 956    5/1989

(Continued)

OTHER PUBLICATIONS

Thierry, A.R. et al in FASEB J. vol. 6, pp. 572-579, 1993.*

(Continued)

*Primary Examiner*—Gollamudi S. Kishore
(74) *Attorney, Agent, or Firm*—Robins & Pasternak LLP

(57) ABSTRACT

Methods for administering mitomycin C to a multi-drug resistant cell and for reducing the toxicity of the compound are described. In the methods, mitoymic C is provided in the form of a prodrug conjugate, where the drug is linked to a hydrophobic moiety, such as a lipid, through a cleavable dithiobenzyl linkage. The dithiobenzyl linkage is susceptible to cleavage by mild thiolysis, resulting in release of mitomycin C in its original form. The linkage is stable under nonreducing conditions. The prodrug conjugate can be incorporated into liposomes for administration in vivo and release of mitomycin C in response to endogenous in vivo reducing conditions or in response to administration of an exogenous reducing agent.

10 Claims, 24 Drawing Sheets

U.S. PATENT DOCUMENTS

| | | | |
|---|---|---|---|
| 4,179,337 | A | 12/1979 | Davis et al. |
| 4,766,106 | A | 8/1988 | Katre et al. |
| 4,902,502 | A | 2/1990 | Nitecki et al. |
| 4,917,888 | A | 4/1990 | Katre et al. |
| 4,935,465 | A | 6/1990 | Garman |
| 5,103,556 | A | 4/1992 | Filip et al. |
| 5,395,619 | A | 3/1995 | Zalipsky et al. |
| 5,560,923 | A * | 10/1996 | Rahman et al. ............. 424/450 |
| 5,631,018 | A | 5/1997 | Zalipsky et al. |
| 5,648,090 | A * | 7/1997 | Rahman et al. ............. 424/450 |
| 5,891,468 | A | 4/1999 | Martin et al. |
| 6,180,095 | B1 | 1/2001 | Greenwald et al. |
| 6,342,244 | B1 | 1/2002 | Zalipsky |
| 6,365,179 | B1 | 4/2002 | Zalipsky et al. |
| 6,605,299 | B2 | 8/2003 | Zalipsky |
| 6,638,500 | B1 | 10/2003 | El-Tayar et al. |
| 6,849,270 | B2 | 2/2005 | Zalipsky |
| 6,984,396 | B2 | 1/2006 | Zalipsky et al. |
| 2004/0161455 | A1 | 8/2004 | Gabizon et al. |
| 2004/0213579 | A1 | 10/2004 | Zalipsky et al. |

FOREIGN PATENT DOCUMENTS

| | | |
|---|---|---|
| EP | 0 317 957 | 5/1989 |
| EP | 0 317 957 A2 | 5/1989 |
| EP | 0 510 197 A1 | 10/1992 |
| EP | 0 898 968 | 3/1999 |
| FR | 2 254 336 | 7/1975 |
| JP | 1113391 | 5/1989 |
| WO | WO 9736904 | 10/1997 |
| WO | WO 98/16201 | 4/1998 |
| WO | WO 99/29302 | 6/1999 |
| WO | WO00/64483 | 11/2000 |
| WO | WO 00/64484 | 11/2000 |
| WO | WO00/64484 | 11/2000 |
| WO | WO01/26629 | 4/2001 |
| WO | WO02/26265 | 4/2002 |
| WO | WO03/053409 | 7/2003 |
| WO | WO2004/110497 | 12/2004 |

OTHER PUBLICATIONS

Warren et al in Cancer Research, vol. 52, 3241-3245, 1992.*
Ellman, G.I., Arch. Biochem. Biophys., 82:70-77 (1959).
Grassetti and Murray, Arch. Biochem. Biophys., 119(1):41-49 (1967).
Brois, S.J., et al., *J. Amer. Chem. Soc.* 92(26):7629-7631 (1970).
Dittmer, J.C., et al., *J. Lipid Res.* 126-127 (1964).
Gaber, M., et al., *Pharmaceutical Res* 12(10):1407-1416, (1995).
Grice, R., et al., *J. Chem. Soc.* 1947-1954 (1963).
Hirota, S., *International J of Pharmaceutics* 162(1-2):185-194, (1998).
Engman, L., et al., Bioorganic & Medicinal Chemistry 11:5091-5100, (2003).
Johnsson, M., et al., *J of Liposome Res* 9(1):53-79, (1999).
Kaneko, T., et al., *Bioconjugate Chem.* 2(3):133-141 (1991).
Kirpotin, D., et al., *FEBS Letters* 388:115-118, (1996).
Lash, L.H., et al., *Arch. Biochem. Biophys.* 240(2):583-592 (1985).
Mueller, C.E., et al., 322(6):343-350, (1989).
Senter, P.D., et al., *J Org Chem* 55(9):2975-2978, (1990).
Vaage, J., et al., *Cancer* 72(12):3671-3675, (1993).
Vaage, J., et al., *Cancer* 73(5):1478-1484, (1994).
Vaage, J., et al., *International J of Cancer* 51(6)942-948, ().
Veronese, et al., *Applied Biochem. and Biotech.* 141-152 (1985).
Zalipsky, et al., *Biotechnol. Appl. Biochem.* 100-114 (1992).
Zalipsky, et al., *Eur. Polymer. J.* 19(12):1177-1183 (1983).
Zalipsky, et al., *Bioconj. Chem.* 4(4):296-299 (1993).
Zalipsky, *Bioconj Chem* 10(5):703-707, (1999).
Vaage, J., et al., *Int. J. Cancer* (80): 134-137(1999).
Asai et al., *Biol. Pharm. Bull.*, 21(7):766-771 (1998).
Briddell et al., *Blood*, 102(11):163b-164b (1999).
Database Dissertation Abstracts [Online] Proquest Info & Learning; Woghiren, Clement O. et al.: "Synthesis, Characterization and Conjugation of a Novel Protected Thiol-Polyethylene Glycol: A New Activated Polymer for Reversible Protein Modification (IL-2)" Dialog Accession No. 01367093; Dissertation Abstracts 55(03-B), 1994, p. 866.
Johnson et al., *Chemistry and Biology*, 4(12):939-950 (1997).
Kratz et al., *J. Med. Chemistry*, 45(12):5523-5533 (2002).
Malik et al., *Experimental Hematology*, 28(7, Suppl. 1):106, Abstract No. 237 (2000).
Thorpe et al., *Cancer Res.*, 47(12):5924-5931 (1987).
Vaage et al., *International Journal of Cancer*, 80(1):134-137 (1999).
Worrell et al., *Anticancer Drug Design*, 1(12):179-188 (1986).
Diaz, et al., *Bioconjugate Chem* 9:250-254, (1998).
Vaage, J., et al., *Intl J Cancer* 51(6):942-948, (1992).
Zalipsky, S., et al., 28th International Symposium on Controlled Release of Bioactive Materials and 4th Consumer & Diversified Products Conference, San Diego, CA, Publisher: Controlled Release Society 1:437-438, (2001).

* cited by examiner

METHOD FOR TREATING MULTI-DRUG RESISTANT TUMORS

This application claims the benefit of U.S. Provisional Application No. 60/467,070, filed Apr. 30, 2003 and is a continuation-in-part of U.S. application Ser. No. 10/057,839, filed Jan. 25, 2002, now U.S. Pat. No. 6,984,396 which is a continuation of U.S. application Ser. No. 09/556,610, filed Apr. 21, 2000 now U.S. Pat. No. 6,365,179, which claims the benefit of U.S. Provisional Application No. 60/130,897, filed Apr. 23, 1999. Each of these priority documents are incorporated herein by reference in their entirety.

FIELD OF THE INVENTION

The present invention relates to a method for reducing the cytotoxicity of mitomycin C, and to a method of administering mitomycin C to a multi-drug resistant cell. Mitomycin C is provided in the form of a prodrug conjugate comprised of a hydrophobic moiety linked to the drug via a cleavable linkage. More particularly, the prodrug conjugate is comprised of a lipid linked to the drug via a cleavable linkage, the lipid being incorporated into a liposomal formulation. The prodrug conjugate is cleavable under mild thiolytic conditions in vivo for release of mitomycin C in an unmodified state.

BACKGROUND OF THE INVENTION

Mitomycin is an established chemotherapeutic agent given for several different types of cancer, including breast, stomach, gullet and bladder cancer. The agent acts by cross-linking DNA so the cancer cells are unable to proliferate. When given intravenously to patients, common side effects due to the toxicity include fever, nausea, vomiting, bone marrow depression, and others (HARRISON'S PRINCIPLES OF INTERNAL MEDICINE, Wilson et al., Eds., 12$^{th}$ Editions, Part Eleven,. page 1592, 1991). Drug toxicity is not the only problem associated with chemotherapy. Another problem is drug resistance. Some tumor types, e.g., non-small cell lung cancer and colon cancer, exhibit primary resistance, i.e., absence of response on the first exposure to currently available, conventional chemotherapeutic agents. Other tumor types exhibit acquired resistance, which develops in a number of drug-sensitive tumor types. Drug resistant cancer cells demonstrate two types of acquired drug resistance; cells exhibiting single agent resistance or resistance to single class of anti-cancer drugs with the same mechanism of action. The second type involves cells broadly resistant to several or many chemically diverse anti-cancer drugs with different mechanisms of action. This second type of acquired resistance is known as multi-drug resistance.

Multi-drug resistance is also found in some tumor cells, such as renal and colon tumors, exhibiting primary resistance. That is, in contrast to an acquired multi-drug resistance, certain tumor types are non-responsive to initial treatment with many chemotherapeutic agents.

Multidrug-resistance is often associated with increased expression of a normal gene, the MDR1 gene, for a cell surface glycoprotein, P-glycoprotein, involved in drug efflux. P-glycoprotein expression correlates with a decrease in intracellular drug accumulation; that is, the P-glycoprotein acts as an energy-dependent pump or transport molecule that removes drugs from the cell, preventing the drug from accumulating in the cell.

P-glycoprotein is normally primarily expressed at epithelial and endothelial surfaces and seems to play a role in absorption and/or secretion. It is an active transporter that pumps hydrophobic drugs out of cells, reducing their cytoplasmic concentration and therefore toxicity. In normal cells, P-glycoprotein functions to eliminate toxic metabolites or xenobiotic compounds from the body (Endicott, J. and Ling, V., *Annu. Rev. Biochem.*, 58:137-171, (1989)).

Cancers which express P-glycoprotein include cancers derived from tissues which normally express the MDR1 gene, namely cancers of the liver, colon, kidney, pancreas and adrenal. Expression of the gene is also seen during the course of chemotherapy with multidrug-resistant drugs in leukemias, lymphomas, breast and ovarian cancer, and many other cancers. These cancers initially respond to chemotherapy, but when the cancer relapses, the cancer cells frequently express more P-glycoprotein. There are cancers derived from tissues which do not normally express P-glycoprotein but in which P-glycoprotein expression increases during the development of the cancer. One example is chronic myelogenous leukemia, which when it goes into blast crisis, expresses more P-glycoprotein irrespective of the previous treatment history (Gottesman, M. M. *Cancer Research*, 53:747-754 (1993)).

The MDR1-encoded P-glycoprotein pump recognizes and transports many different substances, including most natural product anti-cancer drugs such as doxorubicin, daunorubicin, vinblastine, vincristine, actinomycin D, paclitaxel, teniposide and etoposide (Gottesman, M. et al., *Current Opinion in Genetics and Development*, 6:610-617 (1996)). More generally, the drugs often involved in multidrug-resistance are alkaloids or antibiotics of plant or fungal origin, and they include the vinca alkaloids, anthracyclines, epipodophyllotoxins and dactinomycin. Cross-resistance to alkylating agents such as melphalan, nitrogen mustard, and mitomycin C is occasionally observed (Endicott, J. and Ling, V., *Annu. Rev. Biochem.*, 58:137-171, (1989)). Clearly, multidrug-resistance in cancer cells limits successful chemotherapy and suggests a poor patient prognosis.

Liposomes are closed lipid vesicles used for a variety of therapeutic purposes, and in particular, for carrying therapeutic agents to a target region or cell by systemic administration of liposomes. Liposomes having a surface grafted with chains of water-soluble, biocompatible polymer, in particular polyethylene glycol, have become important drug carries. These liposomes offer an extended blood circulation lifetime over liposomes lacking the polymer coating. The grafted polymer chains shield or mask the liposome, thus minimizing nonspecific interaction by plasma proteins. This in turn slows the rate at which the liposomes are cleared or eliminated in vivo since the liposome circulate unrecognized by macrophages and other cells of the reticuloendothelial system. Furthermore, due to the enhanced permeability and retention effect (Maeda H. et al., *J. Controlled Release*, 65(1-2):271 (2000)), the liposomes tend to accumulate in sites of damaged or expanded vasculature, e.g., tumors, sites of inflammation.

An extended blood circulation time is often desired to allow systemically administered liposomes to reach a target region, cell or site. For example, a blood circulation lifetime of greater than about 12 hours is preferred for liposomal-therapy to a tumor region, as the liposomes must systemically distribute and then extravasate into the tumor region.

It would be desirable to provide a formulation of mitomycin C that can be taken up by multi-drug resistant cells. It would also be desirable to formulate a liposome composition having a long blood circulation lifetime and capable of retaining an entrapped drug for a desired time, yet able to release the drug on demand. It would also be desirable to provide a formulation of mitomycin C that is as efficacious as the drug in free form, yet has a reduced systemic toxicity. Furthermore, it would be desirable to release the cytotoxic mitomycin C in response to the endogenous conditions in the tumor.

SUMMARY OF THE INVENTION

Accordingly, it is an object of the invention to provide a liposomal formulation of mitomycin C that offers a reduced toxicity relative to the drug in free form, and which can be taken up by multi-drug resistant cells. That is, mitomycin C unable to accumulate in multi-drug resistant cells when administered in free form is able to accumulate in such cells when administered in the form of a prodrug conjugate incorporated into the liposomal formulation described herein.

In one aspect, the invention includes a method for reducing the in vivo cytotoxicity of mitomycin C, comprising providing mitomycin C in the form of a liposome composition comprised of a vesicle-forming lipid and of between about 1 to about 30 mole percent of a conjugate having the general form:

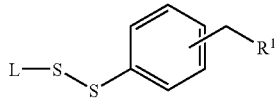

wherein L is a hydrophobic moiety suitable for incorporation into a liposomal lipid bilayer, $R^1$ is mitomycin C covalently attached to the dithiobenzyl moiety, and where orientation of the $CH_2R^1$ group is selected from the ortho position and the para position.

In one embodiment, mitomycin C is covalently attached by a urethane (carbamate) linkage.

In another embodiment, L is selected from the group consisting of cholesterol, a diacylglycerol, and a phospholipid.

In another embodiment, mitomycin C is covalently linked to the dithiobenzyl moiety to form a conjugate having the structure:

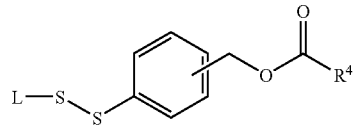

wherein $R^4$ represents a residue of mitomycin C, where the secondary amine in the aziridine moiety of mitomycin C forms a urethane linkage between the dithiobenzyl and mitomycin C.

In another aspect, the invention includes a method for administering mitomycin C to a multi-drug resistant cell, comprising providing mitomycin C in the form of a liposome composition comprised of a vesicle-forming lipid and of between about 1 to about 30 mole percent of a conjugate having the general form:

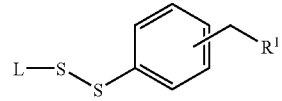

wherein L is a hydrophobic moiety suitable for incorporation into a liposomal lipid bilayer, $R^1$ is mitomycin C covalently attached to the dithiobenzyl moiety, and where orientation of the $CH_2R^1$ group is selected from the ortho position and the para position.

These and other objects and features of the invention will be more fully appreciated when the following detailed description of the invention is read in conjunction with the accompanying drawings.

DETAILED DESCRIPTION OF THE INVENTION

I. Definitions

The phrase "hydrophobic moiety suitable for incorporation into a liposomal lipid bilayer" intends any material comprising a hydrophobic portion capable of being integrated with the hydrophobic bilayer region of a liposomal lipid bilayer. Such hydrophobic moieties are typically lipids, including amphipathic lipids having a hydrophobic lipid tail and a hydrophilic polar head, such as phospholipids and diacylglycerols. Triglycerides, sterols, derivatives of phospholipids, diacylglyerols, sterols and triglycerides and other lipids derived from a natural source or synthetically prepared are also contemplated.

The term "residue" as in "therapeutic drug residue" intends a drug molecule that has been reacted to form an linkage with another molecule where at least one atom of the drug molecule is replaced or has been sacrificed to from the linkage.

Figure 6A:
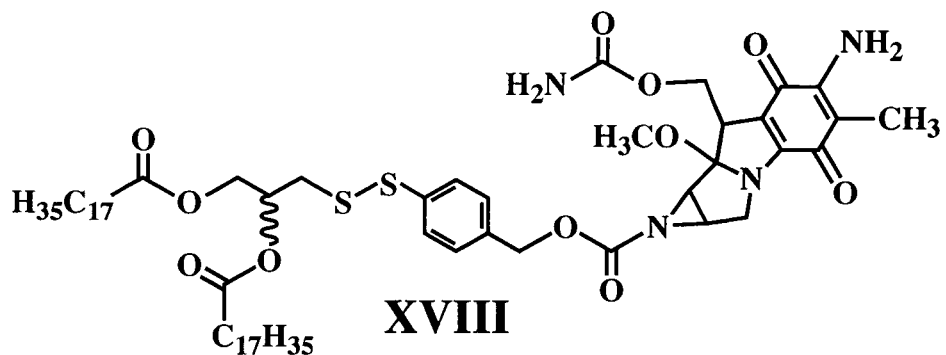
FIGS. 6A-6C show the structures of three lipid-dithiobenzyl-mitomycin-C conjugates, para-distearoyl-DTB-mitomycin-C (FIG. 6A), para-dipalmitoyl-DTB-mitomycin-C (FIG. 6B) and ortho-dipalmitoyl-DTB-mitomycin-C (FIG. 6C)

Reference to "lipid-DTB-mitomycin C" is to Compound XVIII of FIG. 6A.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like.

The following abbreviations are used herein: PEG, poly(ethylene glycol); mPEG, methoxy-PEG; DTB, dithiobenzyl; DSPE, distearoyl phosphatidylethanolamine; HSPC, hydrogenated soy phosphatidylcholine; MMC, mitomycin C.

II. Coniuqate Composition and Method of Preparation

In one aspect, the invention includes a conjugate of the form:

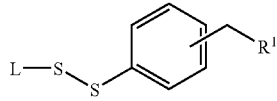

wherein L is a hydrophobic moiety suitable for incorporation into a liposomal lipid bilayer, $R^1$ represents a therapeutic drug residue covalently attached to the dithiobenzyl moiety, and where orientation of the $CH_2R^1$ group is selected from the ortho position and the para position. The hydrophobic moiety, L, is typically a lipid such as a diacylglycerol, a sterol, a phospholipid, derivatives of these lipids, other naturally-occurring lipids and their synthetic analogs.

In the conjugate, a therapeutic drug is attached to the dithiobenzyl moiety by a covalent linkage, thereby forming a drug residue, represented by $R^1$ in the structure. The linkage will vary according to the drug and the reaction chemistry, as will be appreciated by those of skill in the art. In preferred embodiments, the therapeutic drug is covalently attached to the diithiobenzyl moiety by a linkage selected from the group consisting of urethane, amine, amide, carbonate, thio-carbonate, ether and ester.

A urethane linkage takes the form of $O(C=O)NH—R^4$ or $O(C=O)N=R^4$, where $R^4$ represents the therapeutic drug residue. For example, a drug containing a primary or secondary amine, such as mitomycin C, mitomycin A, bleomycin and therapeutic polypeptides to name a few, is reacted to from a urethane linkage with the amine moiety in the drug.

A carbonate linkage takes the form of $O(C=O)O—R^4$, where $R^4$ represents the drug residue and the carbonate linkage derives from a phenol or alcohol or hydroxyl moiety in the drug. A thio-carbonate takes the form of $O(C=O)S—R^4$, where $R^4$ represents the drug residue and the linkage derives from a moiety in the drug. Exemplary drugs having such a moiety for reaction with dithiobenzyl alcohol to form a carbonate linkage include fluorodeoxyuridine, iododeoxyuridine, etoposide, AZT, acyclovir, vidarabine, arabinosyl cytosine, pentostatin, quinidine, mitoxantrone and atropine.

An ester linkage takes the form of $O(C=O)—R^4$, where $R^4$ represents the drug residue. The linkage derives from reaction with a carboxylic acid moiety in the therapeutic drug, and an example of a conjugate having an ester linkage between chlorambucil and dithiobenzyl is described below. Methotrexate is another example of a drug capable of forming an ester linkage with the dithiobenzyl moiety of the conjugate.

Conjugates having a urethane, carbonate or ester linkage attaching the drug to the dithiobenzyl moiety can generally be represented by the following structure:

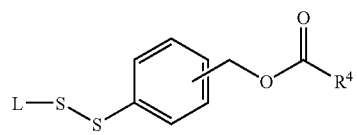

wherein $R^4$ represents a residue of the therapeutic drug.

In another embodiment, the conjugate includes an ether linkage, which takes the form of $O—R^4$, where $R^4$ represents the therapeutic drug residue. The linkage typically derives from reaction with an alcohol functionality on the drug.

An amine linkage is of the form $N=R^4$, where $R^4$ represents the drug residue and the linkage is a direct attachment with the $CH_2$ moiety of the dithiobenzyl with a N in the drug. A conjugate with the drug 5-fluorouracil where an amine linkage is formed is one example, set forth in U.S. Pat. No. 6,342,244. An amide linkage can also be formed with a peptide as the therapeutic agent, where the free carboxyl of an amino acid residue, such as an aspartic acid or glutamic acid, is condensed with dithiobenzylamine.

An amide linkage takes the form of $NH(C=O)—R^4$, where $R^4$ represents the drug residue.

Figure 1:
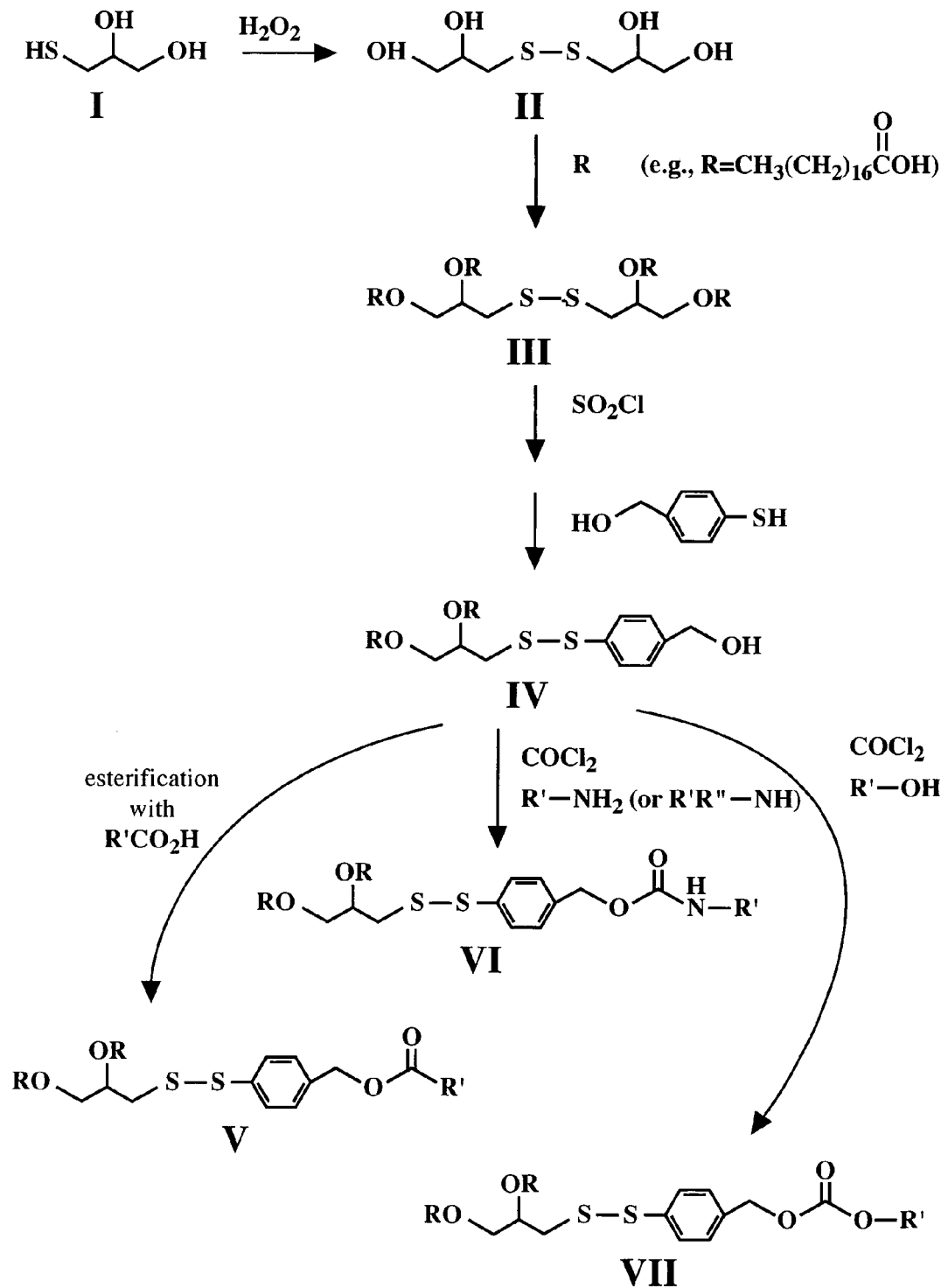
FIG. 1 shows a synthetic reaction scheme for preparation of para-diacyldiglycerol-dithiobenzylalcohol for further reaction with amine-, hydroxy- or carboxyl-containing drugs.

FIG. 1 shows a synthetic reaction scheme for preparation of exemplary conjugates in accord with the invention. In this embodiment, synthesis of an intermediate compound, para-diacyldiglyceroldithiobenzalcohol (Compound IV), is prepared for further reaction with a selected therapeutic drug. Compound IV is prepared, as described in Example 1, by reacting 3-mercapto-1,2-propanediol (Compound I) with hydrogen peroxide to form rac-3,3'-dithiobis(1,2-propanediol) (Compound II). Rac-3,3'-dithiobis(1,2-propanediol) is acylated with a hydrophobic moiety R. For example, R can be a fatty acid having from about 8 to about 24 carbon atoms. Example 1 details the reaction procedure where R is stearic acid. In another embodiment, R is a fatty acid having from about 12 to about 22 carbon atoms. Acylation of Compound II yields Rac-3,3'-dithiobis(1,2-propanedistearoyl) (Compound III), which is reacted with sulfuryl chloride and 4-mercaptobenzalcohol to form the desired intermediate product, para-diacyldiglycerol-dithiobenzalcohol (Compound IV). Compound IV is readily reacted with a drug containing a reactive carboxyl moiety (R'CO$_2$H) to form a lipid-dithiobenzyl (DTB)-drug conjugate where the drug is joined to the DTB via an ester linkage (Compound V). Compound IV is also readily reacted with a drug containing a reactive amine moiety (R'—NH$_2$) to yield a lipid-DTB-drug conjugate where the drug is joined to the DTB by a urethane linkage (Compound VI). Compound IV is also readily reacted with a drug containing a reactive hydroxyl moiety (R'OH) to form a lipid-DTB-drug conjugate where the drug is joined to the DTB by a carbonate linkage (Compound VII).

A variety of drugs are contemplated for use in the conjugate of the invention. In particular, the invention contemplates drugs having an amine (NH or NH$_2$), carboxyl, sulfhydryl or hydroxyl moiety suitable for reaction. As used herein, "suitable for reaction" implies that the drug has one of the recited moieties capable of reacting with the dithiobenzyl moiety, in the form of, for example, dithiobenzyl alcohol. Exemplary drugs include 5-fluorouracil, which has an NH group suitable for reaction, chlorambucil, which has a reactive carboxyl and mitomycin C, which has a reactive amine (aziridine group). Synthesis of conjugates using 5-fluorouracio and chlorambucil are set forth in U.S. Pat. No. 6,365,179; synthesis of conjugates using mitomycin C is discussed with respect to FIGS. 2-6. Other exemplary drugs contemplated for use include mitomycin C, mitomycin A, bleomycin, doxorubicin, daunorubicin, fluorodeoxyuridine, iododeoxyuridine, etoposide, AZT, acyclovir, vidarabine, arabinosyl cytosine, pentostatin, quinidine, atropine, chlorambucil, methotrexate, mitoxantrone and 5-fluorouracil. It will be appreciated that polypeptides, aminoglycosides, alkaloids are all also suitable for use in the invention.

Example 1 also details the reaction conditions for preparation of ortho-diacyldiglyceroldithiobenzalcohol, which can serve as a intermediary compound to form the conjugate.

Figure 2A:
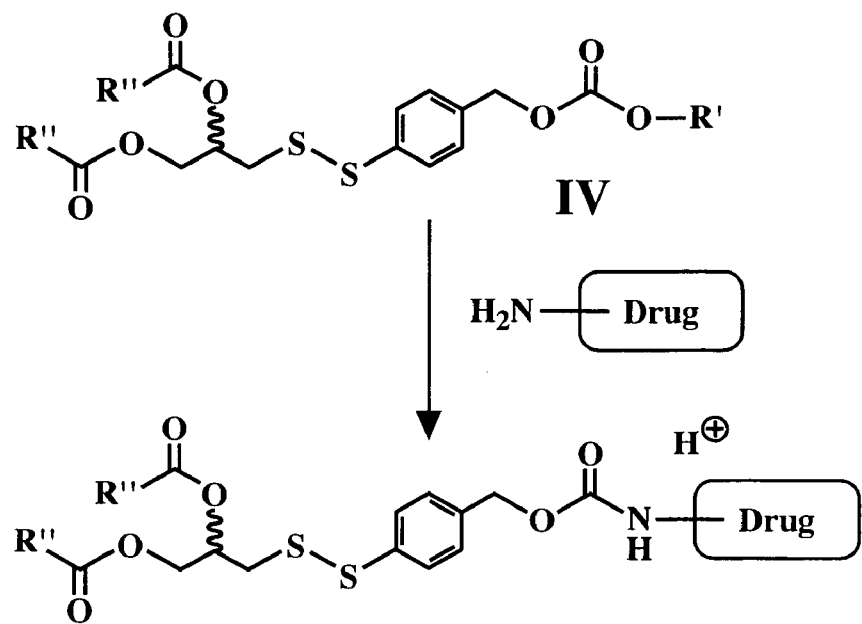
FIG. 2A shows a general reaction scheme for attachment of an amino-containing drug to a reactive diacyldiglycerol-dithiobenzylcarbonate.
Figure 2B:
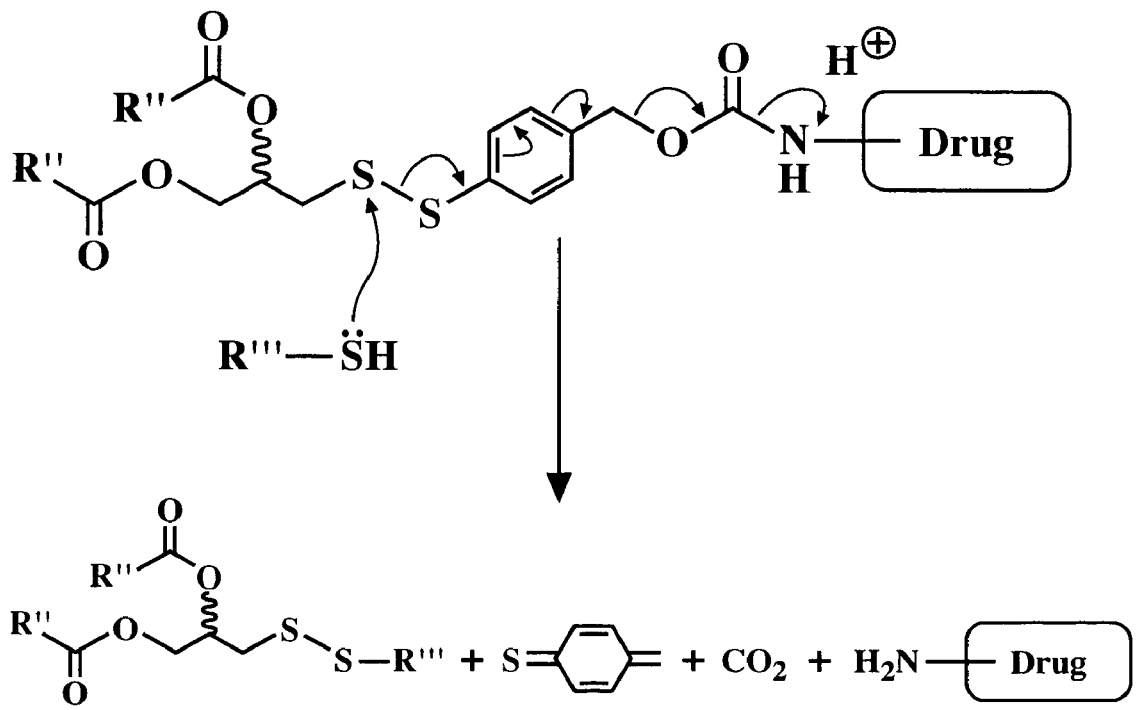
FIG. 2B shows the products after thiolytic cleavage of the conjugate in FIG. 2A.

FIGS. 2A-2B show preparation of a lipid-DTB-drug conjugate (FIG. 2A), and thiolytic cleavage of the conjugate in the presence of a reducing agent (FIG. 2B). As shown in FIG. 2A, Compound VII of FIG. 1 where the hydrophobic moiety R is derived from a fatty acid R''(CO)OH, such as stearic acid (CH$_3$(CH$_2$)$_{16}$CO$_2$H), is reacted with an amine-containing drug, H$_2$N-drug, in the presence of phosgene (COCl$_2$). This reaction yields the lipid-DTB-drug conjugate illustrated in FIG. 2A. The conjugate, upon exposure to reducing conditions, i.e., a reducing agent such as cysteine or glutathione, decomposes to yield the products shown in FIG. 2B. As shown, thiolytic cleavage of the conjugate results in regeneration of the drug in an unmodified, natural state. This is a desirable feature, since, as will be shown below, the drug in conjugate can be readily incorporated into liposomes for administration in vivo to a subject. Further, the drug in the form of the conjugate is not toxic, as will also be shown below. After administration and upon exposure to endogenous reducing agents or exposure to an exogenous reducing agent, the conjugate decomposes to yield the drug in its native state and with biological activity.

Figure 3A:
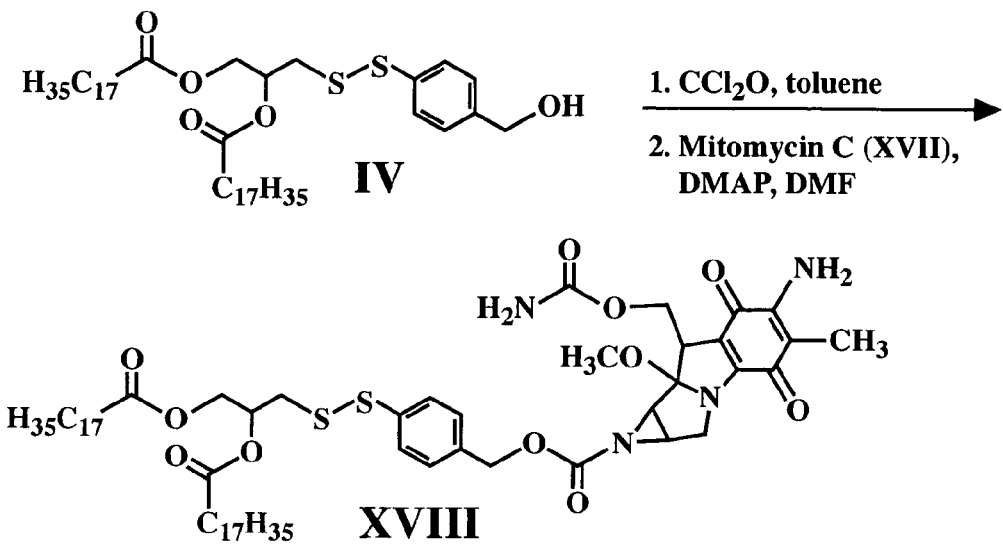
FIG. 3A shows a synthetic reaction scheme for preparation of a diacyldiglycerol-dithiobenzyl-mitomycin-C conjugate.

FIG. 3A shows the synthesis of the mitomycin C prodrug conjugate. In the reaction scheme shown, mitomycin C (Compound XVII, FIG. 3B), a drug containing a reactive amine moiety, is reacted with para-diacyl-diglycerol-dithiobenzalalcohol (Compound IV) in the presence of phosgene to form a diacyldiglycerol-dithiobenzyl-mitomycin-C conjugate (Compound XVIII). Details of the synthesis are provided in Example 2.

Figure 3B:
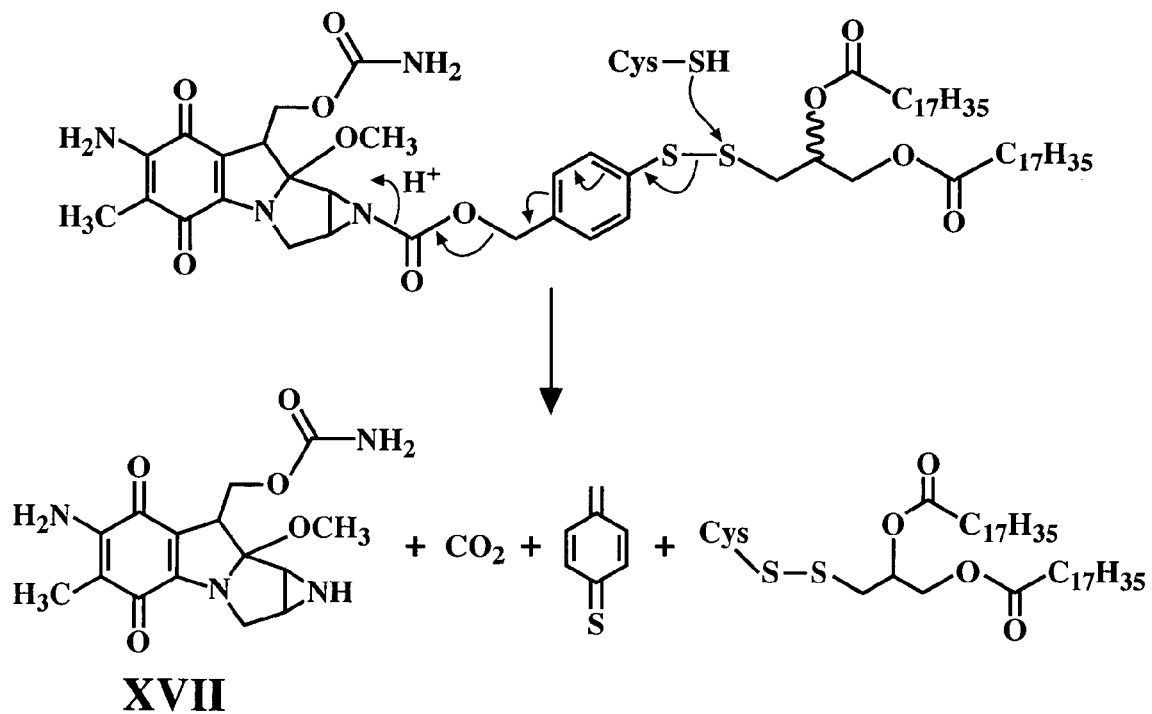
FIG. 3B shows the products after thiolytic cleavage of the conjugate in FIG. 3A.

FIG. 3B shows the thiolytic decomposition of a diacyl-diglycerol-DTB-mitomycin-C conjugate. In the presence of a reducing agent, the conjugate decomposes to regenerate mitomycin C (Compound XVII) and the other products shown.

As noted above, the hydrophobic moiety in the conjugate can be selected from any number of hydrophobic moieties, e.g., lipids. In one embodiment, a diacyldiglycerol lipid can be used to form conjugates having the structure:

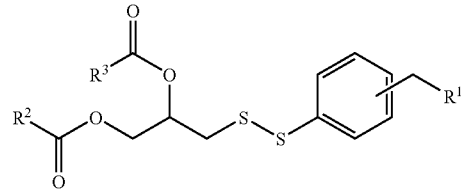

wherein R$^2$ and R$^3$ are hydrocarbons having between about 8 to about 24 carbon atoms.

Figure 4:
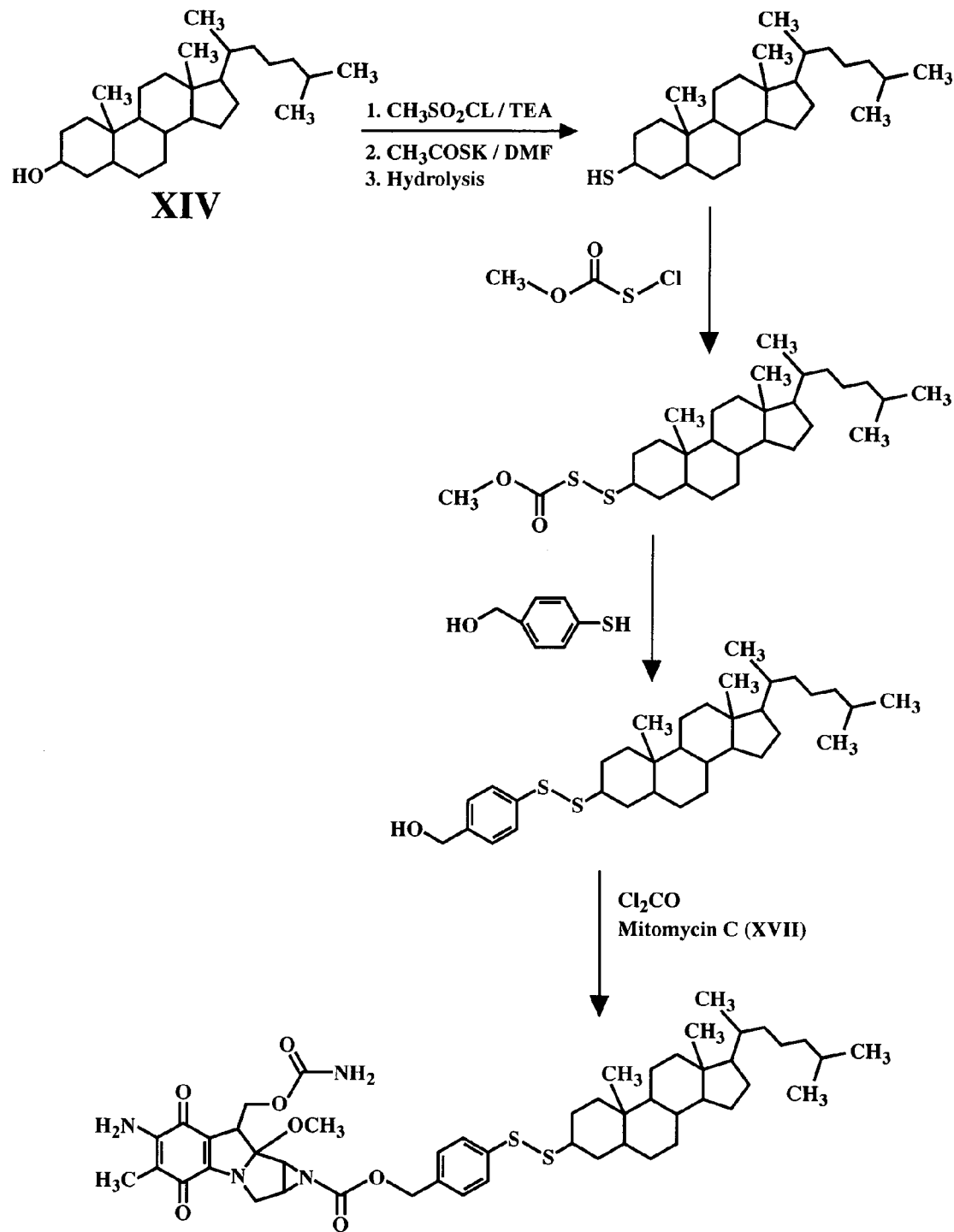
FIG. 4 shows a synthetic reaction scheme for preparation of a cholesterol-dithiobenzyl-mitomycin-C conjugate.

In addition to diacylglycerols as the hydrophobic moiety, other lipids are contemplated. FIG. 4 shows another embodiment where cholesterol is used as the hydrophobic moiety in the conjugate. Cholesterol (Compound XIV) is reacted with methanesulfonyl chloride in dichloromethane in the presence of triethylamine (TEA). The resulting intermediate is then converted into the thiol derivative and ultimately into the principal dithiobenzyl alcohol, which is used to link mitomycin C in a similar fashion as described above for diacylglycerol.

Figure 5:
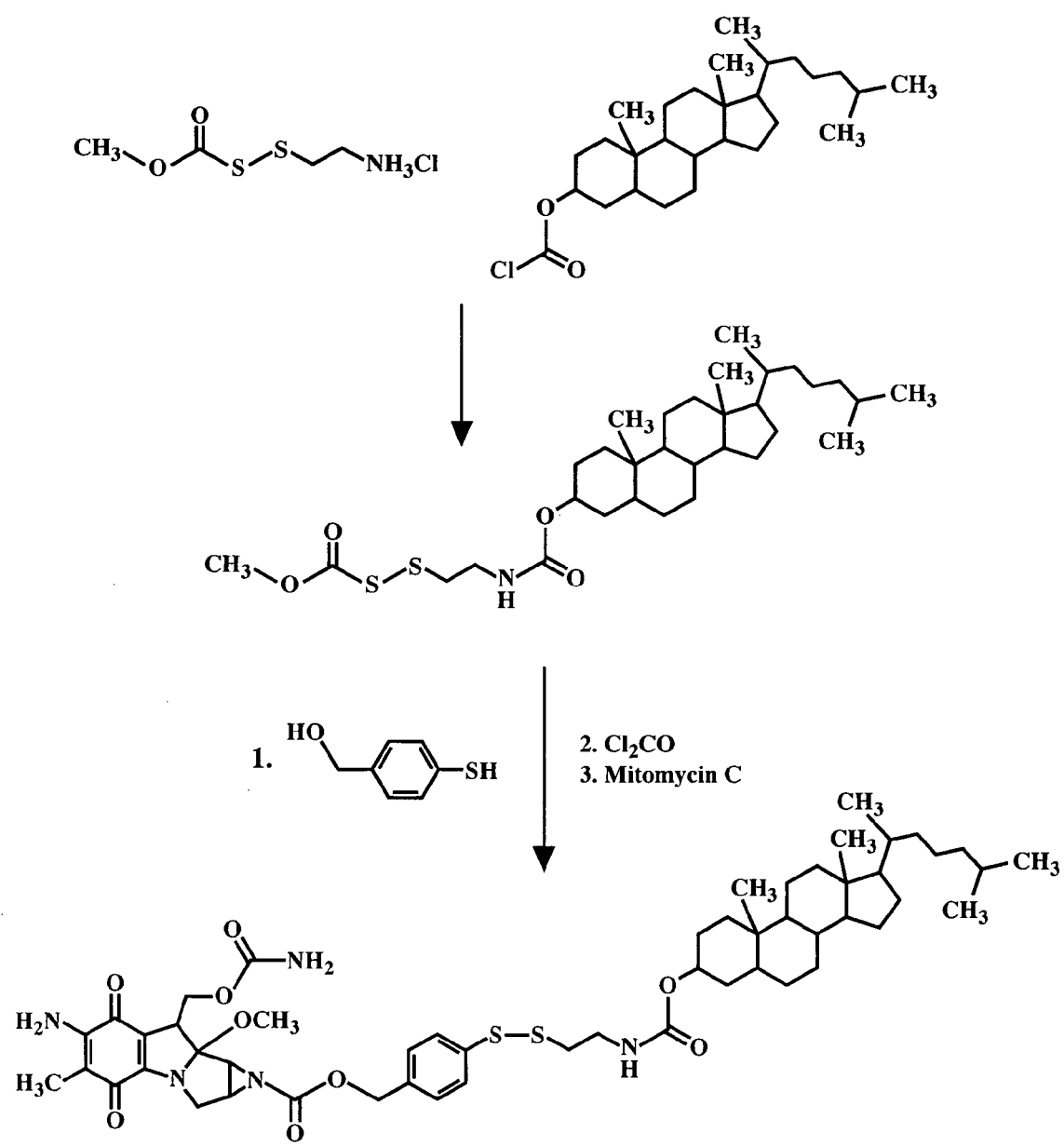
FIG. 5 shows another synthetic reaction scheme for preparation of a cholesterol-dithiobenzyl-mitomycin-C conjugate.

An alternative reaction scheme for preparation of a cholesterol-DTB-mitomycin-C conjugate is shown in FIG. 5. Methoxycarbonyldithioethyl amine is directly reacted with cholesterol chloroformate forming a urethane linkage. Then mercaptobenzylalcohol is used to obtain the DTB-cholesterol compound. Mitomycin C is linked as described above and in Example 2.

Figure 6B:
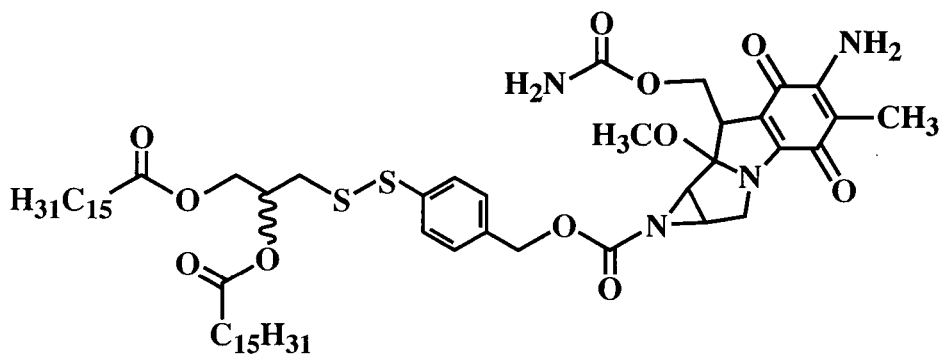
Figure 6C:
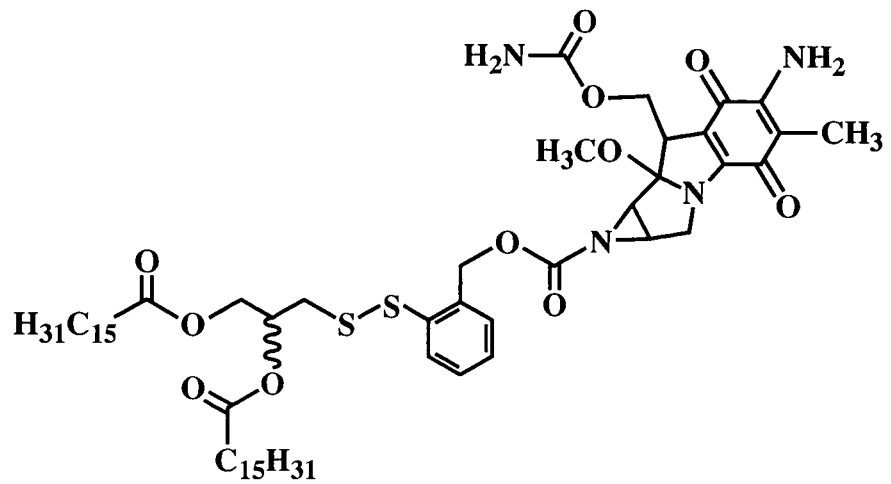

In studies performed in support of the invention, described below, the conjugate prepared as described in FIG. 3A, Compound XVII, para-distearoyl-DTB-mitomycin C, was used. For ease of reference, this conjugate is shown in FIG. 6A. It is to be appreciated that other diacyl lipids, such as a dipalmitoyl lipid, can be used, and FIG. 6B shows a para-dipalmitoyl-DTB-mitomycin C conjugate. It will also be appreciated that the conjugate can also have an isomeric linkage. This is evident by the ortho-dipalmitoyl-DTB-mitomycin C conjugate as shown in FIG. 6C.

III. Preparation of Liposomes Comprising Conjugate

In the method of the invention, the mitomycin C prodrug conjugate is provided in the form of a liposome composition comprised of a vesicle-forming lipid and the mitomycin C prodrug conjugate. Liposomes are closed lipid vesicles used for a variety of therapeutic purposes, and in particular, for carrying therapeutic agents to a target region or cell by systemic administration of liposomes. In particular, liposomes having a surface coating of hydrophilic polymer chains, such as polyethylene glycol (PEG), are desirable as drug carries as these liposomes offer an extended blood circulation lifetime over liposomes lacking the polymer coating. The polymer acts as a barrier to blood proteins thereby preventing binding of the protein and recognition of the liposomes for uptake and removal by macrophages and other cells of the reticuloendothelial system.

Liposomes, according to the invention, include a conjugate in combination with a lipid, which in one embodiment is a vesicle-forming lipid, and, optionally, other bilayer components. "Vesicle-forming lipids" are lipids that spontaneously form bilayer vesicles in water. The vesicle-forming lipids preferably have two hydrocarbon chains, typically acyl chains, and a polar head group. There are a variety of synthetic vesicle-forming lipids and naturally-occurring vesicle-forming lipids known in the art where the two hydrocarbon chains are typically from about 12 to about 24 carbon atoms in length, and have varying degrees of unsaturation. Examples include the phospholipids, such as phosphatidylcholine (PC), phosphatidylethanolamine (PE), phosphatidic acid (PA), phosphatidylinositol (PI), and sphingomyelin (SM). A preferred lipid for use in the present invention is hydrogenated soy phosphatidylcholine (HSPC). Another preferred family of lipids are diacylglycerols. These lipids can be obtained commercially or prepared according to published methods.

The vesicle-forming lipid may be selected to achieve a degree of fluidity or rigidity, to control the stability of the liposome in serum, and to control the rate of release of an entrapped agent in the liposome. Liposomes having a more rigid lipid bilayer, or a liquid crystalline bilayer, can be prepared by incorporation of a relatively rigid lipid, e.g., a lipid having a relatively high phase transition temperature, e.g., up to about 80° C. Rigid lipids, i.e., saturated, contribute to greater membrane rigidity in the lipid bilayer. Other lipid components, such as cholesterol, are also known to contribute to membrane rigidity in lipid bilayer structures.

Lipid fluidity is achieved by incorporation of a relatively fluid lipid, typically one having a lipid phase with a relatively low liquid to liquid-crystalline phase transition temperature, e.g., at or below room temperature (about 20-25° C.).

The liposome can also include other components that can be incorporated into lipid bilayers, such as sterols. These other components typically have a hydrophobic moiety in contact with the interior, hydrophobic region of the bilayer membrane, and a polar head group moiety oriented toward the exterior, polar surface of the membrane.

Another lipid component in the liposomes of the present invention, is a vesicle-forming lipid derivatized with a hydrophilic polymer. In this lipid component, a derivatized lipid results in formation of a surface coating of hydrophilic polymer chains on both the inner and outer lipid bilayer surfaces. Typically, between about 1-20 mole percent of the derivatized lipid is included in the lipid composition.

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. The polymers may be employed as homopolymers or as block or random copolymers.

A preferred hydrophilic polymer chain is polyethyleneglycol (PEG), preferably as a PEG chain having a molecular weight between about 500 to about 10,000 Daltons, preferably between about 1,000 to about 5,000 Daltons. Methoxy or ethoxy-capped analogues of PEG are also preferred hydrophilic polymers. These polymers are commercially available in a variety of polymer sizes, e.g., from about 12 to about 220,000 Daltons.

Liposomes of the present invention include typically between about 1 and about 30 mole percent of the lipid-DTB-drug conjugate, preferably between about 5 and about 30 mole percent, more preferably between about 5 and about 20 mole percent. In studies performed in support of the invention, liposomes comprised of the vesicle-forming lipid hydrogenated soy phosphatidylcholine (HSPC), distearoyl phosphatidylethanolamine derivatized with methoxy-polyethylene glycol (mPEG-DSPE) and the conjugate shown in FIG. 6A, para-distearoyl-DTB-mitomycin C (Compound XVIII) were prepared as described in Examples 4A-4B. One of the liposome formulations included cholesterol (Example 4A), with the lipids HSCP/cholesterol/mPEG-DSPE/para-distearoyl-DTB-mitomycin C (Compound XVIII) present at a molar ratio of 60/30/5/5. A second formulation, which contained no cholesterol, was prepared and characterized (Example 4B). In this formulation, the lipids HSCP/mPEG-DSPE/para-distearoyl-DTB-mitomycin C (Compound XVII) were present at a molar ratio of 90/5/5.

IV. In vitro Characterization of Liposomes Containing a Conjugate

A. In vitro Drug Release

Liposomes were prepared as described in Examples 4A4B and were characterized in vitro to determine the rate of release of mitomycin C following exposure to reducing agent. For the in vitro studies, reducing conditions were induced by addition of cysteine, typically at a concentration of about 150 μM, to the test medium. It will be appreciated that in vivo, endogenous reducing conditions may be sufficient to effect thiolytic decomposition of the lipid-DTB-drug conjugate for release of the drug. It is further contemplated that reducing conditions in vivo can be artificially induced by administration of a suitable reducing agent, such as cysteine or glutathione.

The liposome formulations, e.g., HSPC/cholesterol/mPEG-DSPE/conjugate Compound XVIII (hereinafter the "cholesterol-containing formulation") and HSPC/mPEG-DSPE/conjugate Compound XVIII (hereinafter the "cholesterol-free liposome formulation") were incubated at 37° C. in the presence of 150 μM cysteine for 24 hours. Samples were withdrawn at selected time points and analyzed by high performance liquid chromatography (HPLC) to quantify the amount of conjugate and of free mitomycin C. The HPLC conditions are described in Example 5.

Figure 7A:
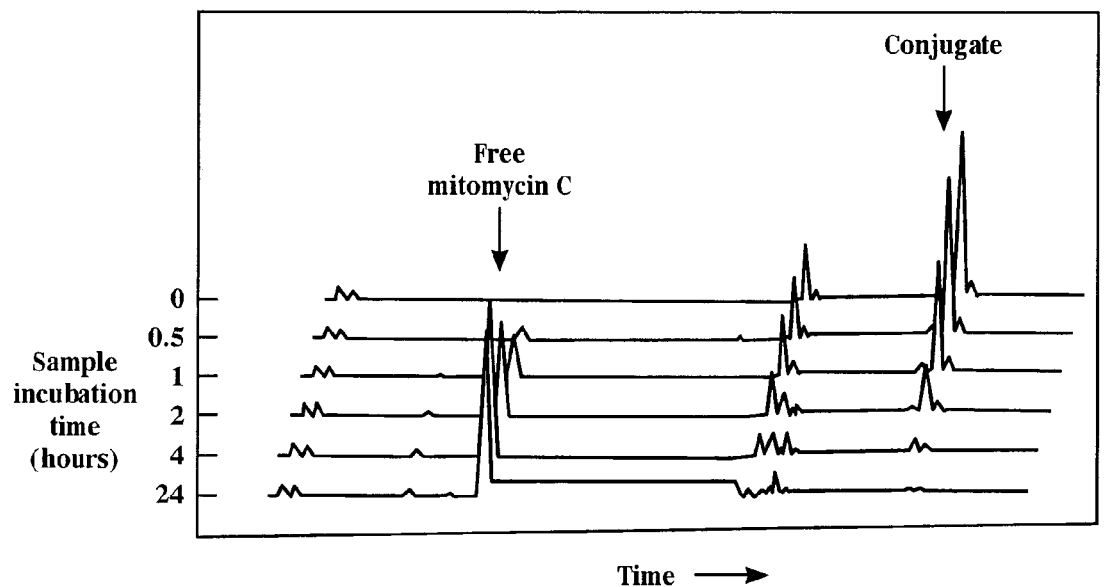
FIGS. 7A-7B are HPLC chromatograms for liposomes comprised of HSPC/mPEG-DSPE/lipid-DTB-mitomycin C (FIG. 7A) and HSPC/cholesterol/mPEG-DSPE/lipid-DTB-mitomycin C (FIG. 7B), where each figure shows a series of chromatograms as a function of time of incubation of the liposomes in the presence of cysteine.
Figure 7B:
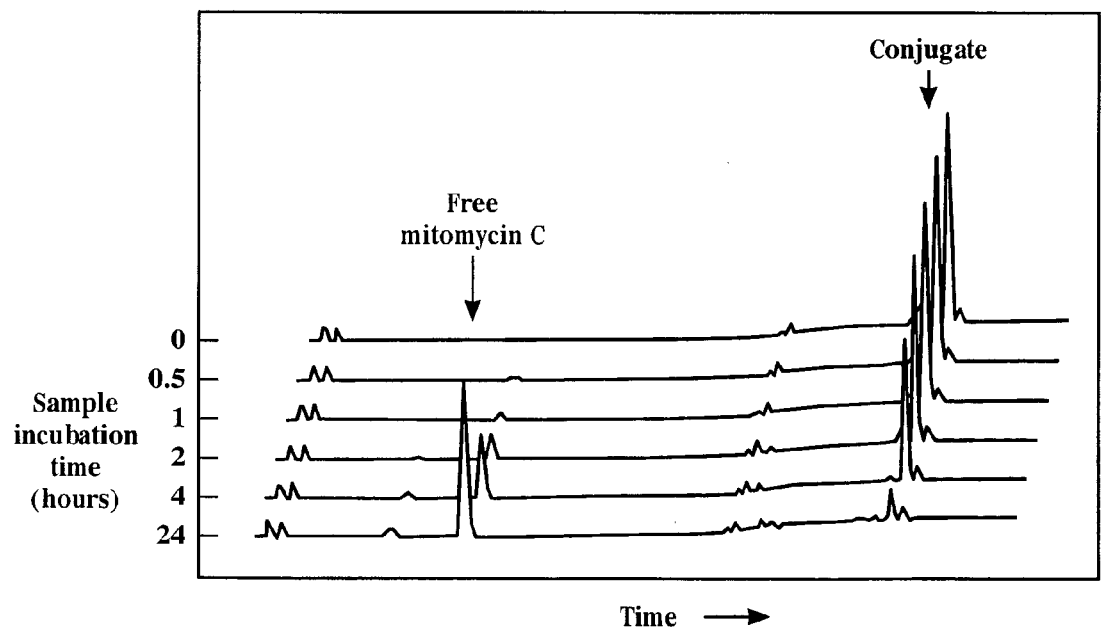

FIGS. 7A-7B show HPLC chromatograms for two liposome formulations. In FIG. 7A, the results for the cholesterol-free liposome formulation are shown. At time zero, there is no detectable free mitomycin C and all measurable drug is in the form of a lipid-DTB-drug conjugate that is liposome bound. As the incubation time increases, the amount of mitomycin C released from the liposomes and detectable in free form increases, with a corresponding decrease in the presence of conjugate-bound mitomycin C.

FIG. 7B shows the results for the liposome formulation containing cholesterol. In the first sample taken at time zero, there was no detectable free mitomycin C. After 1 hour of incubation in 150 μM cysteine, a small amount of free drug was detected, indicating decomposition of the liposome-bound lipid-DTB-mitomycin conjugate. In comparison with FIG. 7A, liposomes containing cholesterol yield a slower conjugate decomposition rate and accordingly slower release of the drug.

Figure 8:
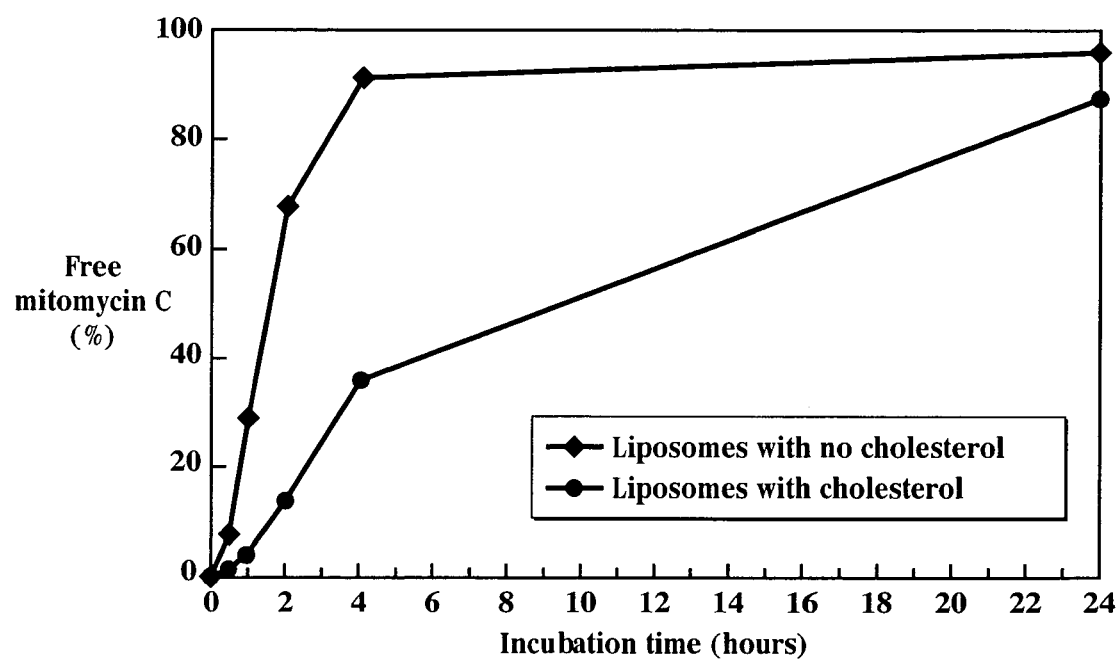
FIG. 8 is a plot showing the percent of mitomycin C released from liposomes comprised of HSPC/mPEG-DSPE/lipid-DTB-mitomycin C (closed diamonds) and HSPC/cholesterol/mPEG-DSPE/lipid-DTB-mitomycin C (closed circles) as a function of time of incubation in the presence of cysteine.

FIG. 8 is a plot showing the percent of mitomycin C. released from the two liposome formulations, as determined from the chromatograms in FIGS. 7A-7B. The cholesterol-free liposomes (closed diamonds) had a higher rate of release than the liposomes containing cholesterol (closed circles). More than 50% of the mitomycin C was released from the liposome-bound conjugate after 2 hours for the cholesterol-free formulation. For both formulations, greater than 80% of the drug was released at the end of the 24 hour incubation period.

Figure 9A:
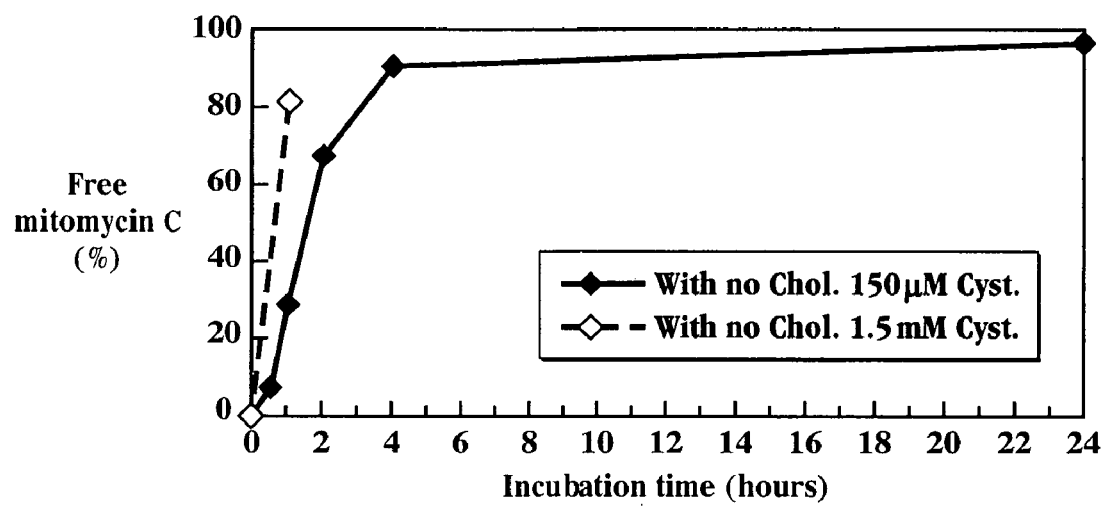
FIGS. 9A-9B are plots showing the percent of mitomycin C released from liposomes comprised of HSPC/mPEG-DSPE/lipid-DTB-mitomycin C (FIG. 9A) and HSPC/cholesterol/mPEG-DSPE/lipid-DTB-mitomycin C (FIG. 9B) as a function of time of incubation in the presence of cysteine at concentrations of 150 μM (closed symbols) and at 1.5 μM (open symbols)
Figure 9B:
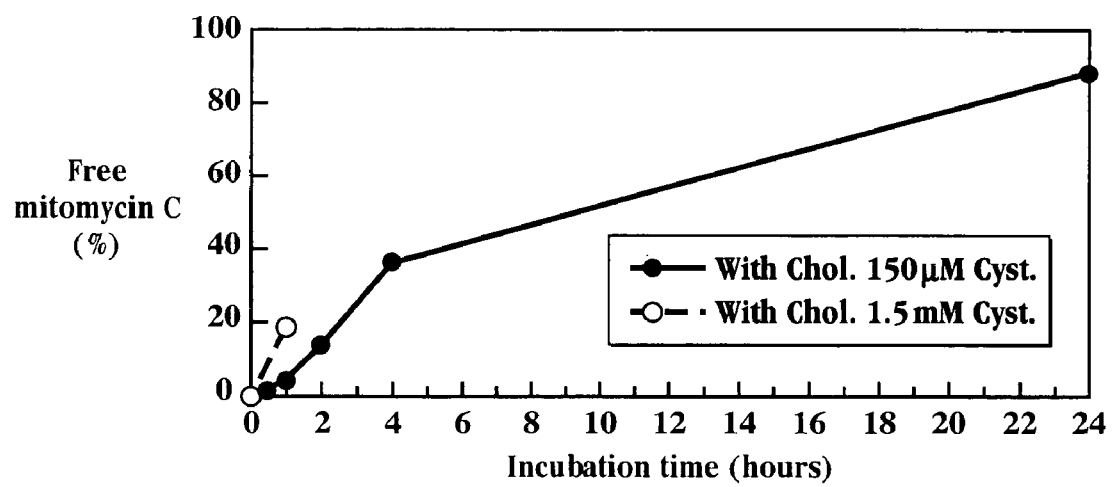

In another study, the two liposome formulations were incubated in 1.5 mM cysteine. Analysis was done as described in Example 5 and the results are shown in FIGS. 9A-9B. FIG. 9A shows the percent of mitomycin C released from the lipid-DTB-drug conjugate incorporated into the cholesterol-free liposomes (HSPC/PEG-DSPE/lipid-DTB-mitomycin C). The percent release during incubation with 150 μM are also shown (closed diamonds) for comparison. As seen, incubation at a higher concentration of reducing agent (1.5 mM, open diamonds) causes an increase in the rate of conjugate decomposition and rate of drug release.

FIG. 9B shows the results for the liposome formulation containing cholesterol. Liposomes incubated in 1.5 mM (open circles) have a significantly higher decomposition rate than the same liposomes incubated in 150 μM cysteine (closed circles).

B. In vitro Cytotoxicity

The in vitro cytotoxicity of liposomes containing the lipid-DTB-mitomycin C conjugate (Compound XVIII) was evaluated using M-109 cells, a mouse lung carcinoma line. As described in Example 6, M109 cells were incubated in the presence of free mitomycin C or liposomes containing the distearoyl-DTB-mitomycin C conjugate. Liposomes prepared as described in Examples 4A-4B with the molar ratios specified in Example 6A were tested. Cysteine at concentrations of 150 μM, 500 μM and 1000 μm was added to some of the test cells to effect thioytic decomposition of the conjugate and release of mitomycin C.

IC50 values were taken as the drug concentration which caused a 50% inhibition of the control growth rate ($IC_{50}$), as described in Example 6. The results are shown in Table 1.

teine has no effect on the activity of free mitomycin c and that mitomycin C is released from the conjugate to effectively inhibit cell growth.

Figure 11A:
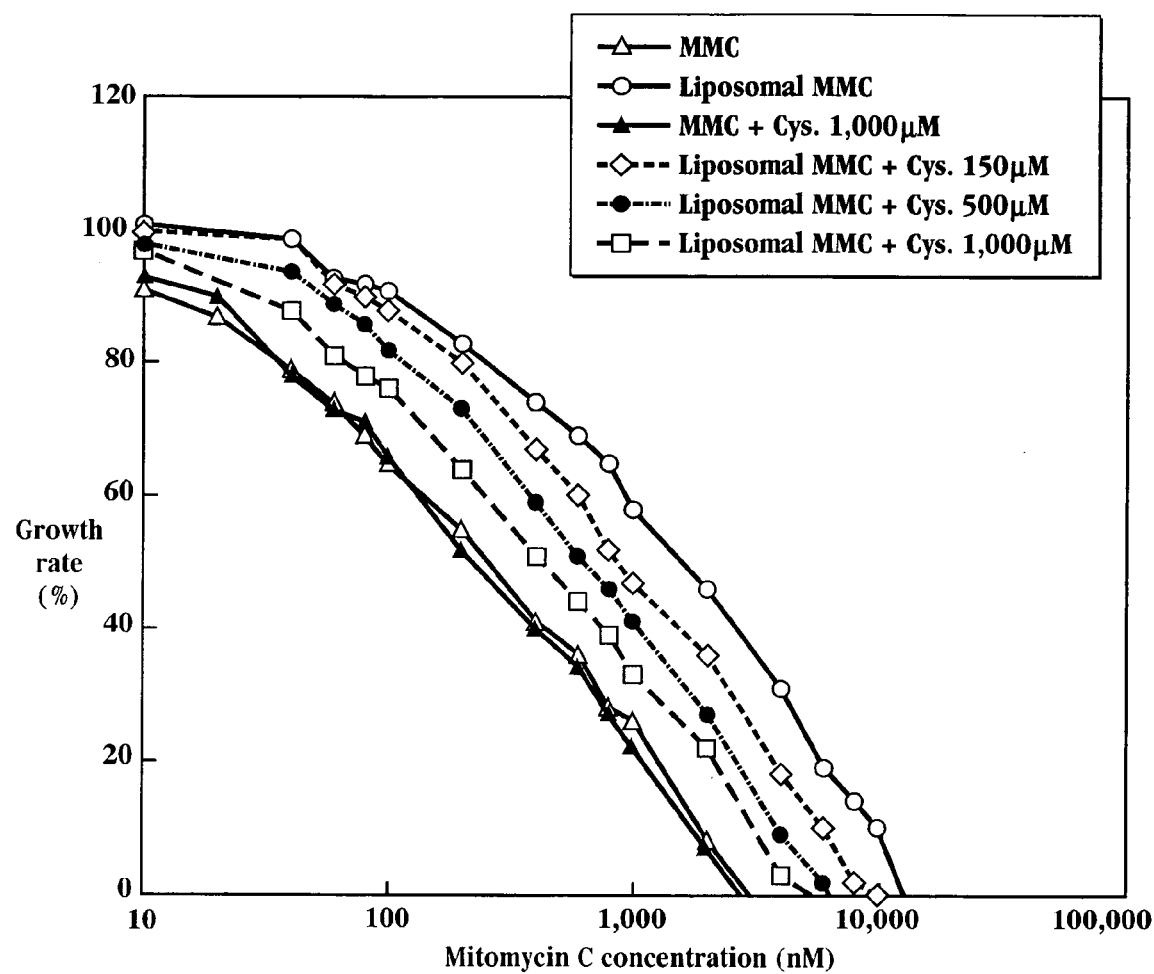
FIG. 11A is a plot of growth rate of M109 cells, expressed as a percentage based on growth of M109 cells in the absence of drug or cysteine, as a function of mitomycin C concentration in nM. Shown are cells treated mitomycin C in free form (open triangles) and with mitomycin C in free form plus 1000 µM cystein (closed triangles). Also shown are cells treated with the liposome formulation comprised of HSPC/PEG-DSPE/lipid-DTB-mitomycin C (open circles) and with the liposome formulation with additional cysteine added at concentrations of 150 µM (open diamonds), 500 µM (closed circles) and 1000 µM (open squares)
Figure 11B:
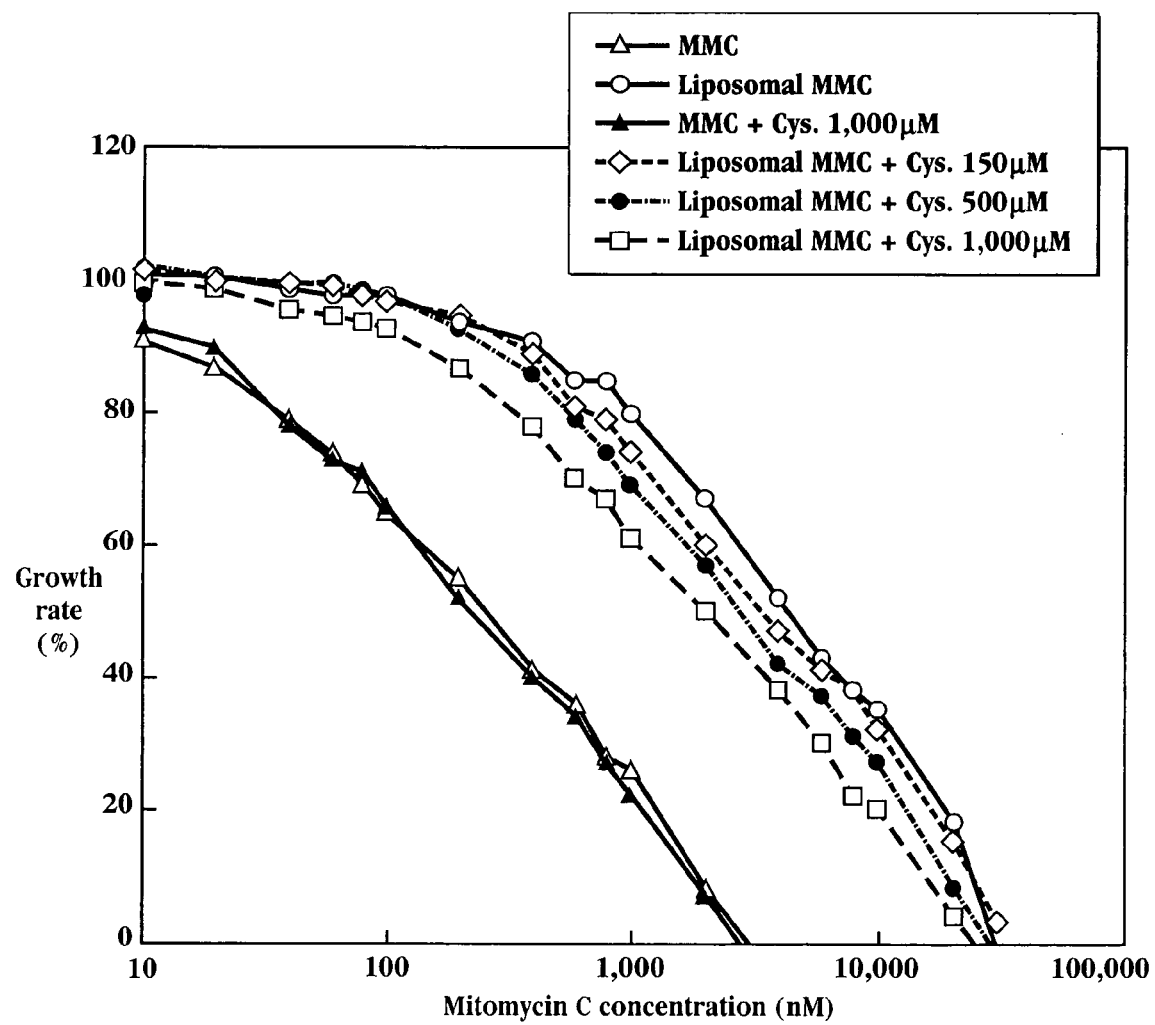
FIG. 11B is a plot of growth rate of M109 cells, expressed as a percentage based on growth of M109 cells in the absence of drug or cysteine, as a function of mitomycin C concentration in nM. Shown are cells treated mitomycin C in free form (open triangles) and with mitomycin C in free form plus 1000 µM cysteine (closed triangles). Also shown are cells treated with the liposome formulation comprised of HSPC/cholesterol/mPEG-DSPE/lipid-DTB-mitomycin C (open circles) and with the liposome formulation with additional cysteine added at concentrations of 150 µM (open diamonds), 500 µM (closed circles) and 1000 µM (open squares)

The in vitro growth rate of M109 mouse carcinoma cells treated with mitomycin C in free form or with mitomycin C in the form a liposome-bound lipid-DTB-drug conjugate is shown in FIGS. 11A-11B. In FIG. 11A the results for the liposome formulation containing no cholesterol are shown. In the plot, the growth rate of M109 cells is expressed as a percentage based on growth of M109 cells in the absence of drug and cysteine and is shown as a function of mitomycin C concentration in nM. The cells treated with mitomycin C in free form (open triangles) and with mitomycin C in free form plus 1000 μM cysteine (closed triangles) exhibit a decrease in growth rate due the toxicity of the drug in free form. Cells treated with the liposome formulation comprised of HSPC/PEG-DSPE/DSPE-DTB-mitomycin C (open circles) and with the liposome formulation with additional cysteine added at concentrations of 150 μM (open diamonds), 500 μM (closed circles) and 1000 μM (open squares) exhibited cell cytotoxicity in a cysteine-dose dependent fashion.

FIG. 11B is a similar plot for the liposome formulation containing cholesterol. The same pattern was observed for cells treated with the liposome composition containing cholesterol plus additional cysteine at concentrations of 150 μM (open diamonds), 500 μM (closed circles) and 1000 μm (open squares). That is, as the concentration of cysteine increased, the cell growth rate decreased. This indicates a cysteine-induced release of mitomycin C in direct correlation with cysteine concentration. In contrast to the liposome formulations, the in vitro growth rate of cells treated with mitomycin C in free form (open triangles) was the same as the growth rate of cells treated with mitomycin C in free form plus 1000 μM cysteine (closed triangles).

TABLE 1

IC50 Values for M109 tumor cells after 72 hour culture with continuous exposure to formulation

| Formulation | Cysteine Concentration | | | |
|---|---|---|---|---|
| | 0 | 150 μM | 500 μM | 1000 μM |
| free MMC[1] | 285 ± 92 | n.d.[4] | n.d. | 300 ± 71 |
| liposomes with cholesterol[2] | 1750 ± 356 | 1140 ± 368 | 650 ± 42 | 510 ± 113 |
| cholesterol-free liposomes[3] | 5400 ± 1414 | 4550 ± 1484 | 3600 ± 1272 | 2550 ± 778 |

Figure 10:
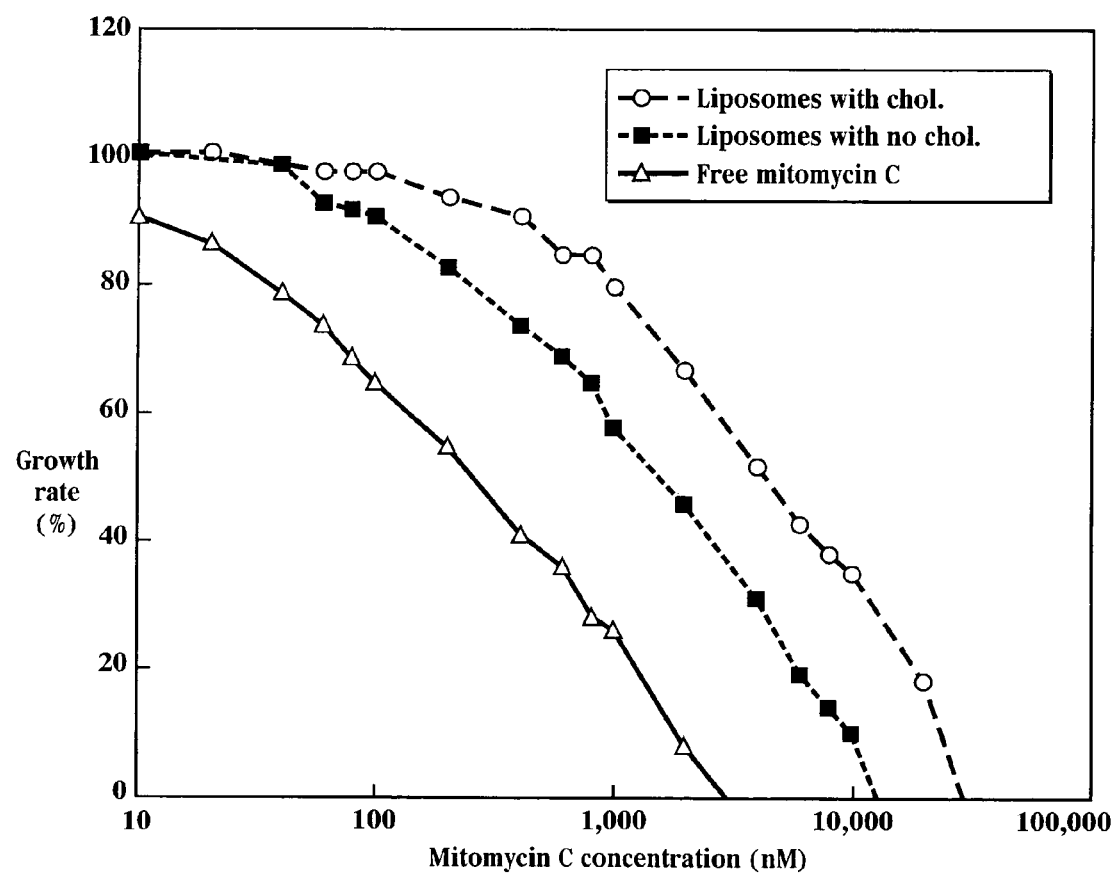
FIG. 10 is a plot of growth rate of M109 cells, expressed as a percentage based on growth of M109 cells in the absence of drug and cysteine, as a function of mitomycin C amount, in nM, for free mitomycin c (open triangles), liposomes comprised of HSPC/mPEG-DSPE/lipid-DTBmitomycin C (closed squares), and liposomes comprised of HSPC/cholesterol/mPEG-DSPE/lipid-DTB-mitomycin C (open circles)
Figure 12:
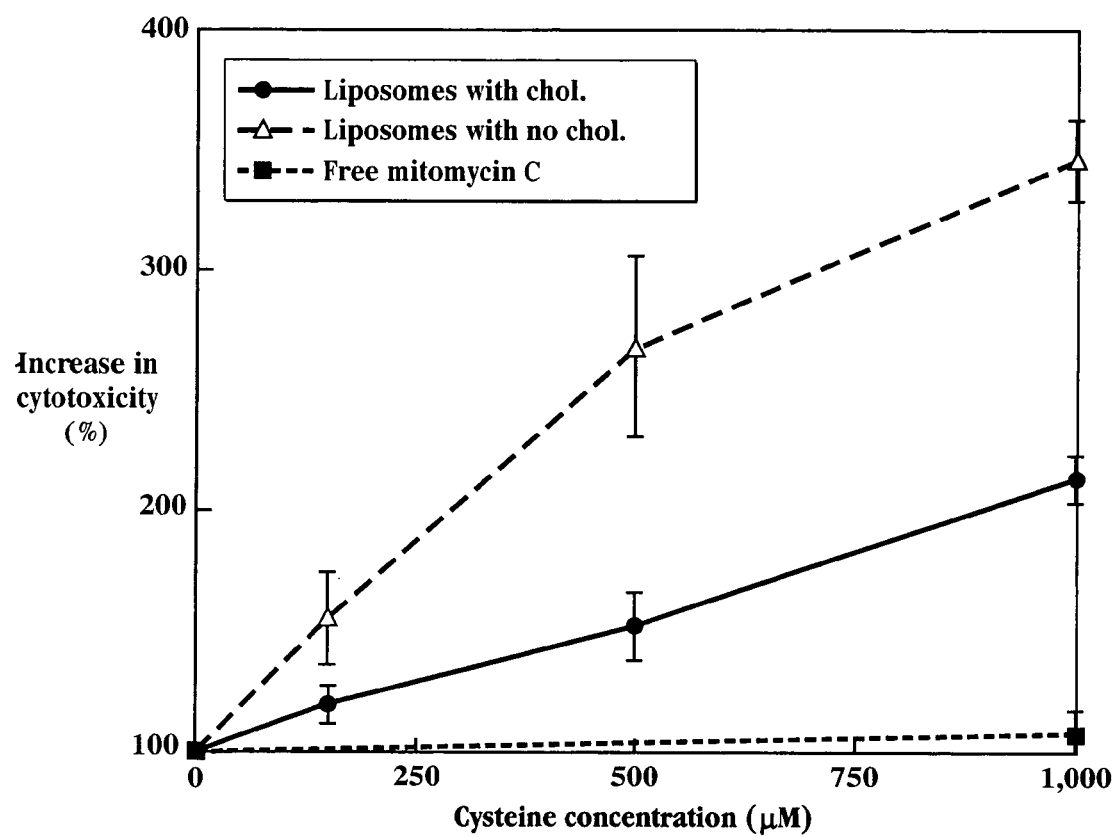
FIG. 12 is a plot showing the percent increase in cytotoxicity (as determined by ($IC50_{no\ cysteine}/IC50_{cysteine}$)×100)) of free mitomycin C (closed squares), mitomycin C associated with liposomes comprised of HSPC/cholesterol/mPEG-DSPE/lipid-DTB-mitomycin C (closed circles), and liposomes comprised of HSPC/mPEG-DSPE/lipid-DTB-mitomycin C (open triangles) to M109 cells in vitro at various concentrations of cysteine.

[1]MMC = mitomycin C
[2]HSPC/cholesterol/mPEG-DSPE/distearoyl-DTB-MMC (90/45/5/5)
[3]HSPC/mPEG-DSPE/distearoyl-DTB-MMC (90/5/5)
[4]n.d. = not done The percent growth rate of M109 mouse carcinoma cells determined from the cytotoxicity studies is shown in FIG. 10. The percent growth rate is expressed as a percentage based on growth rate of M109 cells in the absence of mitomycin C and of cysteine and is shown as a function of mitomycin C concentration, in nM. The growth rate of cells was determined as described in Example 6. As seen, the percent of cell growth rate decreases as the cysteine concentration is increased for both the liposomes containing cholesterol (open circles) and the cholesterol-free liposome formulation (closed squares). It can also be seen that cys- FIG. 12 shows the percent increase in cytotoxicity as a function of cysteine concentration, in μM, of free mitomycin C and of the liposome formulations. Increase in cytotoxicity was determined by the percent drop in IC50, e.g., IC50 in the presence of cysteine relative to IC50 in the absence of cysteine time 100 (($IC50_{no\ cysteine}/IC50_{cysteine}$)×100)). As seen, the percent of cytotoxicity increases significantly as the cysteine concentration is increased for both the liposomes containing cholesterol (open triangles) and the cholesterol-free liposome formulation (closed circles). Cytotoxicity of free mitomycin C (closed squares) is not effected by the presence of cysteine.

The cytotoxicity data shows that the cholesterol-free liposome formulation is more affected by cysteine. The IC50 of the cholesterol-free liposome formulation at certain cysteine concentrations is only 2-fold lower than that of the free drug alone. The liposome formulation containing cholesterol is less cytotoxic than the cholesterol-free liposome formulation. The data also shows that cysteine has no cytotoxic effect of the tumor cells and no effect on the cytotoxicity of free mitomycin C. It is also apparent from the data that cysteine increases in a dose-dependent fashion the cytotoxcity of liposome-bound mitomycin C. Thus, the cytotoxic effects observed for the liposomal formulations are mostly accounted for by cysteine-mediated release of mitomycin C from the lipid-DTB-drug conjugate.

C. In vivo Pharmacokinetics

The in vivo pharmacokinetics of the liposomes containing cholesterol and the cholesterol-free liposome formulation was determined in rats. As described in Example 7, the animals were treated with a single bolus intravenous injection of approximately 0.1 mg/mL mitomycin C in free form or incorporated into liposomes in the form of the lipid-DTB-mitomycin C conjugate in accord with the invention. After injection, blood samples were taken and analyzed for amount of mitomycin C. The results are shown in FIGS. 13A-13B.

Figure 13A:
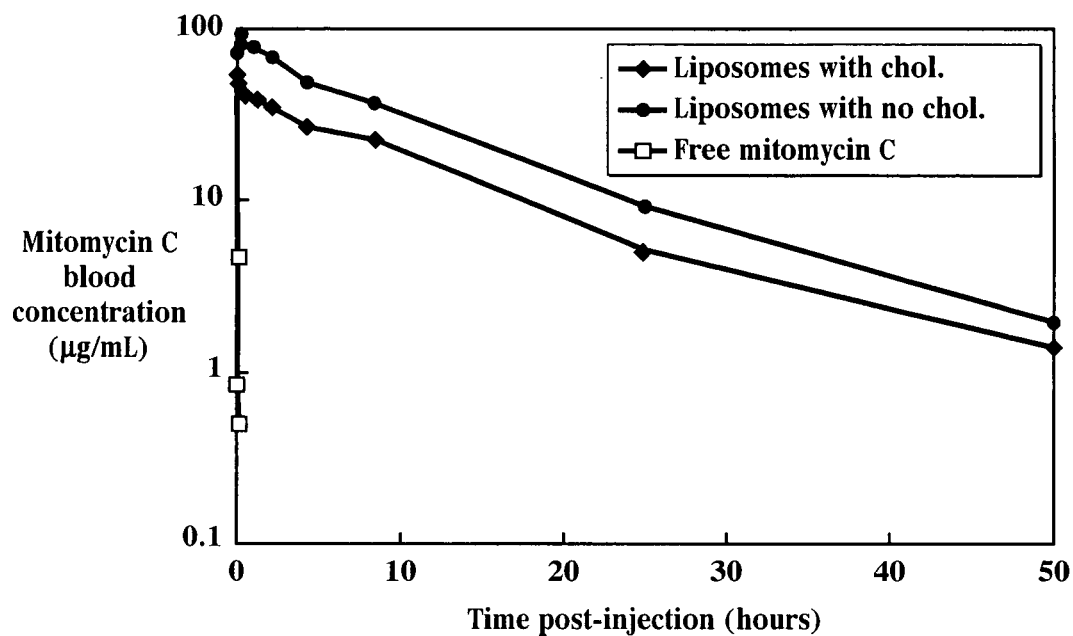
FIG. 13A is a plot showing the concentration of mitomycin C in the blood of rats as a function of time in hours following intravenous injection of free mitomycin C (open squares), liposomes comprised of HSPC/cholesterol/mPEG-DSPE/lipid-DTB-mitomycin C (closed diamonds), and liposomes comprised of HSPC/mPEG-DSPE/lipid-DTB-mitomycin C (closed circles)

FIG. 13A shows the concentration (μg/mL) of mitomycin C in the blood of rats as a function of time in hours following intravenous injection. As seen, free mitomycin C (open squares) administered intravenously in free form is rapidly cleared from the blood. Mitomycin C in the form of a liposome-bound lipid-DTB-drug conjugate remains in circulation for a substantially longer period of time. Mitomycin C associated with liposomes containing cholesterol (closed diamonds) and with cholesterol-free liposomes (closed circles) was detected in the blood at greater than 10 μg/mL for 20-25 hours.

Figure 13B:
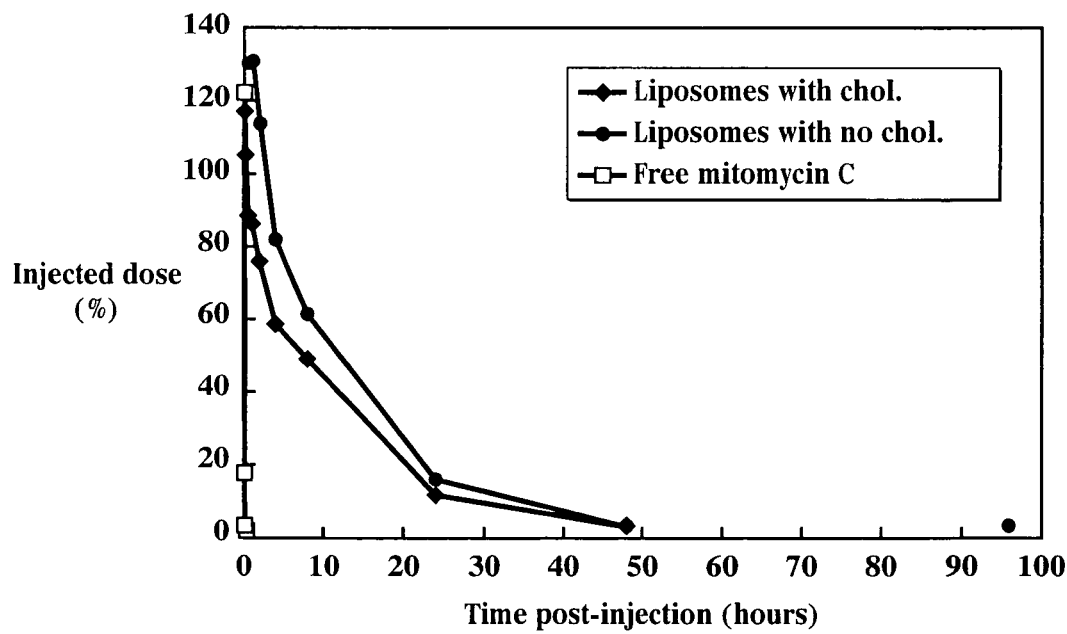
FIG. 13B is a plot showing the percent of injected dose remaining in the blood of rats as a function of time in hours following intravenous injection of free mitomycin C (open squares), liposomes comprised of HSPC/cholesterol/mPEG-DSPE/lipid-DTB-mitomycin C (closed diamonds), and liposomes comprised of HSPC/mPEG-DSPE/lipid-DTB-mitomycin C (closed circles)

FIG. 13B shows the percent of injected dose remaining in the blood as a function of time in hours following intravenous injection of the test formulations. Virtually none of the dose of free mitomycin C (open squares) remains in the blood at time points greater than about 5 minutes. However, at 20 hours after injection of the liposome formulations, about 15-18 percent of the dose of mitomycin C remains in circulation. This indicates the mitomycin C-DTB-lipid conjugate remains stable in the liposome while in circulation and that minimal thiolytic cleavage occurs in plasma. Therefore, this system appear to be compatible with long-circulating liposomes (Stealth®liposomes) which have an extended blood circulation lifetime and enhanced accumulation in tumors.

Figure 14:
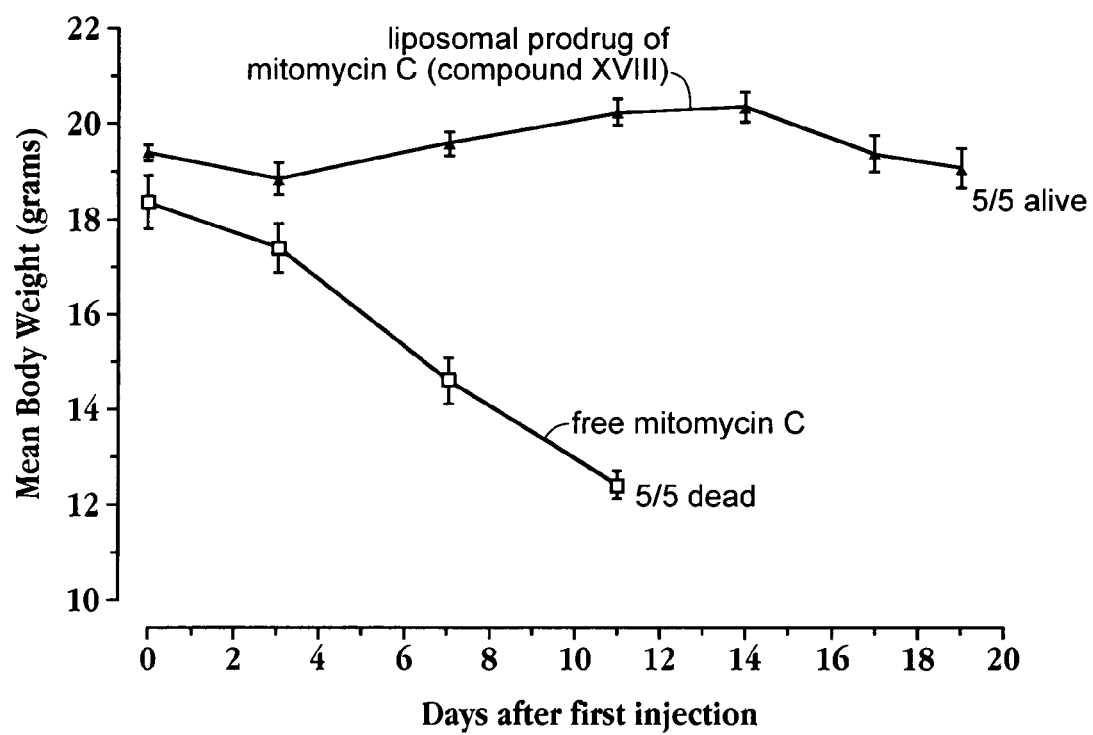
FIG. 14 is a plot showing the mean body weight, in grams, as a function of time, in days, after injection of free mitomycin C (open squares) or of mitomycin C in the form of a liposomes comprised of HSPC/mPEG-DSPE/lipid-DTB-mitomycin C (closed circles)

The reduction in toxicity of mitomycin C when the drug is incorporated into liposomes in the form of a drug-DTB-lipid prodrug conjugate is illustrated in FIG. 14. The liposomes were comprised of HSPC, mPEG-DSPE and para-distearoyl-DTB-mitomycin C in a molar ratio of 90/5/5 (the cholesterol-free formulation described above). Three 10 mg/kg doses of liposomes were injected into female Balb/c mice at a dose of 10 mg drug/kg. Control animals received free mitomycin C, at a dose of 10 mg/kg. The weight of the animals was taken 3, 7, and 11 days after administration of the test substance, as shown in FIG. 14. Animals treated with mitomycin C in free form had a significant loss in body weight and failed to survive past test day 11. Animals receiving mitomycin C in the form of a prodrug conjugate incorporated into liposomes had minimal loss in body weight and all animals were alive at test day 19.

In other studies, liposomes prepared as described in Example 4 were tested in two mouse carcinoma models: an M109 footpad inoculation modes with tumor size as the endpoint, and a C26 intraperitoneal tumor model with survival as the endpoint. Test mice were inoculated with tumor cells (Example 8) and subsequently treated with free mitomycin C or mitomycin C in the form of a prodrug conjugate incorporated into liposomes.

Figure 15A:
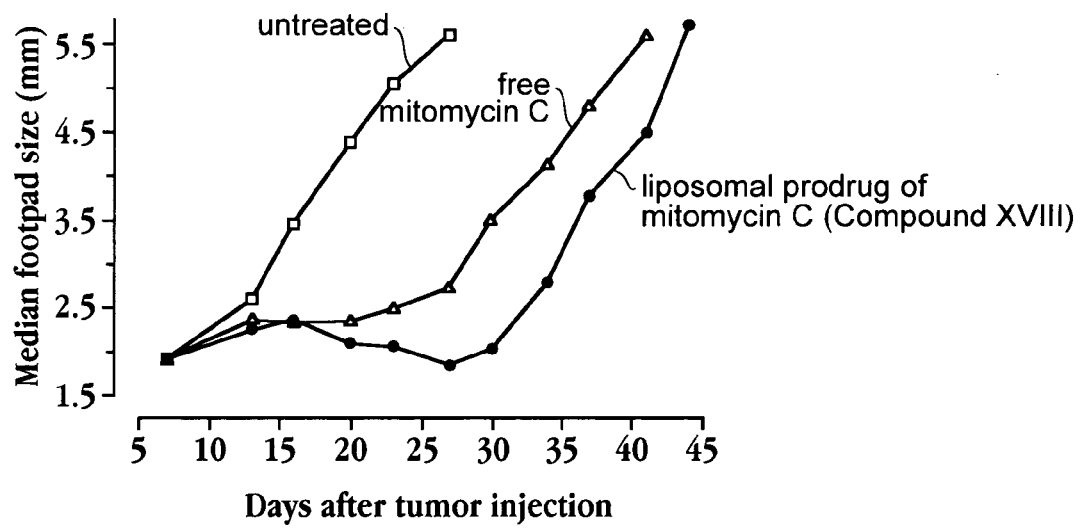
FIG. 15A is a plot showing median footpad size, in mm, as a function of days after inoculation with M109 tumor cells in the paw of mice, where the mice were left untreated (control mice; (open squares)) or were treated with free mitomycin C (open triangles) or with liposomes comprised of HSPC/mPEG-DSPE/lipid-DTB-mitomycin C (closed circles)

For the study illustrated in FIG. 15A, seven days after tumor inoculation (M109 tumor cells) the mice were treated with a test compound intravenously, at a dose of 2 mg/kg. A second intravenous dose was given 13 days after tumor inoculation. The footpad size was measured a regular intervals. The results are shown in FIG. 15A for control mice left untreated (open squares) and for animals treated with free mitomycin C (open triangles) or with the liposomal formulation (HSPC/mPEG-DSPE/lipid-DTB-mitomycin C; closed circles). The tumor size of the untreated control animals increased continuously over the test period. Animals treated with mitomycin C experienced slower tumor growth, with the liposomal formulation providing higher efficacy relative to mitomycin C in free form, as evidenced by a smaller footpad size for animals treated with mitomycin C in the form of a prodrug conjugate incorporated into liposomes.

Figure 15B:
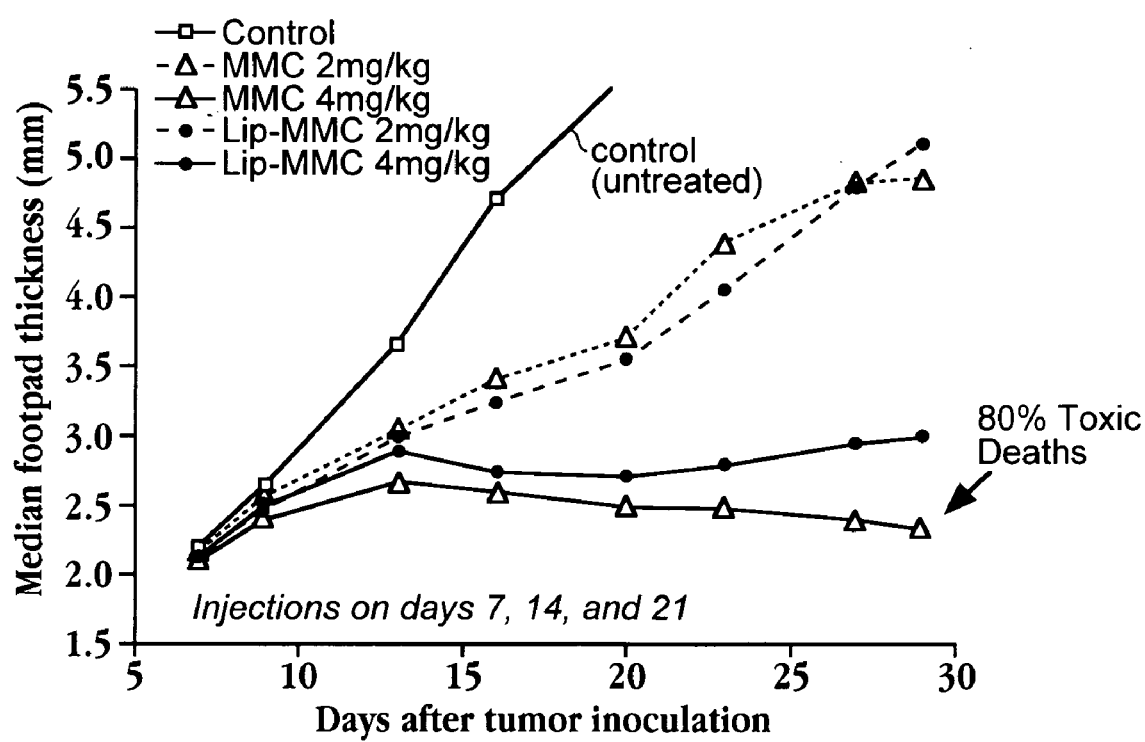
FIG. 15B is a plot showing median footpad size, in mm, as a function of days after inoculation with M109 tumor cells in the paw of mice, where the mice were left untreated (control mice; (open squares)) or were treated with free mitomycin C (open triangles) at 2 mg/kg (dashed line) or 4 mg/kg (solid line), or with liposomes comprised of HSPC/mPEG-DSPE/lipid-DTB-mitomycin C (closed circles) at 2 mg/kg (dashed line) or 4 mg/kg (solid line)

FIG. 15B shows the results from a similar study but with mitomycin C doses of 2 mg/kg and 4 mg/kg. The median footpad size, in mm, was determined as a function of days after inoculation with M109 tumor cells in the paw of mice. Mice left untreated (control mice; (open squares)) had a continuous increase in median footpad thickness. Mice treated with free mitomycin C (open triangles) at 2 mg/kg (dashed line) or 4 mg/kg (solid line) on days 7, 14 and 21, or with liposomes comprised of HSPC/mPEG-DSPE/lipid-DTB-mitomycin C (closed circles) at 2 mg/kg (dashed line) or 4 mg/kg (solid line) on days 7, 14, and 21 had similar tumor growth profiles at corresponding doses. However, animals treated with mitomycin C in free form had a lower survival rate, with an 80% toxic death rate for the animals given a 4 mg/kg dose of free mitomycin C. Thus, mitomycin C administered in the form of a prodrug-conjugate incorporated into liposomes offers similar efficacy as the free drug but at a lower toxicity.

Figure 16A:
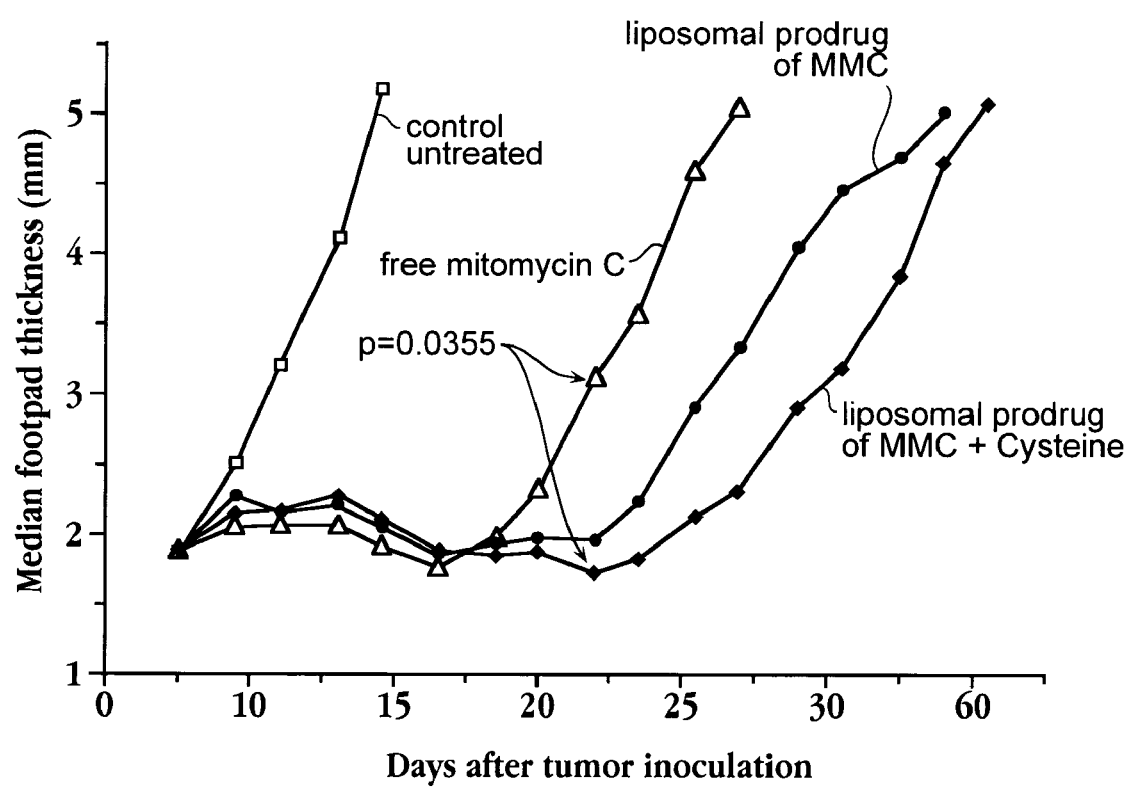
FIG. 16A is a plot showing median footpad size, in mm, as a function of days after inoculation with M109 tumor cells in the paw of mice, where the mice were left untreated (control mice; (open squares)) or were treated with free mitomycin C (open triangles) at 6 mg/kg or with three doses given on days 5, 12, and 19 of liposomes comprised of HSPC/mPEG-DSPE/lipid-DTB-mitomycin C at 6 mg/kg (closed circles, closed diamonds), where animals represented by the closed diamonds received injections of cysteine given on days 6-8, 14-16, and 21-23.
Figure 16B:
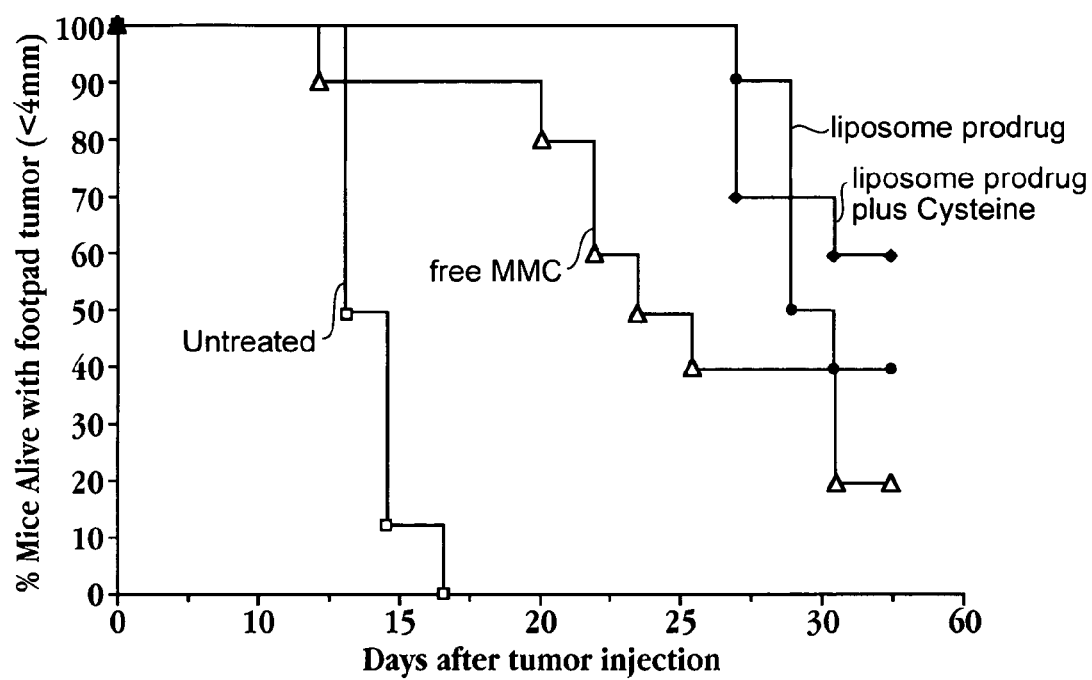
FIG. 16B is a plot showing the percent of mice alive with a footpad tumor size of less than 4 mm, as a function of days after tumor inoculation, for the mice treated as set forth in FIG. 16A.

In another study, the effect of co-administration of exogenous cysteine on the liposomal formulation was evaluated. Mice were inoculated with M109 tumor cells and left untreated or treated with 6 mg/kg mitomycin C in the form of free drug or liposomal-prodrug conjugate 5 days after inoculation. Treatment with 6 mg/kg liposomal prodrug was repeated on days 12 and 19. Treatment with free MMC was not repeated because mice could not tolerate more than one injection of 6 mg/kg. One group of test mice treated with the liposomal-prodrug also received 5 mg/mouse of cysteine. The results are shown in FIGS. 16A-16B. FIG. 16A shows the median footpad size, in mm, as a function of days after inoculation with M109 tumor cells in the paw of mice. The control mice, left untreated, (open squares) had a continual increase in footpad thickness. Mice treated with liposomes comprised of HSPC/mPEG-DSPE/lipid-DTB-mitomycin C at 6 mg/kg on days 5, 12, and 19 (closed circles, closed diamonds) had a slower tumor growth rate than mice treated with free mitomycin C (open triangles). Cysteine was administered subcutaneously on days 6-8, 14-16, and 21-23. Administration of cysteine to mice treated with the liposomal formulation (closed diamonds) provided a higher efficacy, with these test animals showing the slowest increase in footpad thickness, although this difference was not statistically significant.

FIG. 16B shows the percent of mice alive with a footpad tumor size of less than 4 mm, as a function of days after tumor inoculation, for the mice treated as set forth in FIG. 16A. This plot records as descending steps two types of events: deaths (toxic deaths) and tumor measures greater than 4 mm. All of the mice left untreated (open squares) had tumors greater than 4 mm after about test day 23. Mice treated with the liposomal formulation (closed circles, closed diamonds) had tumors less than 4 mm without toxic deaths for a longer period of time than those treated with the drug in free form (open triangles).

Figure 17:
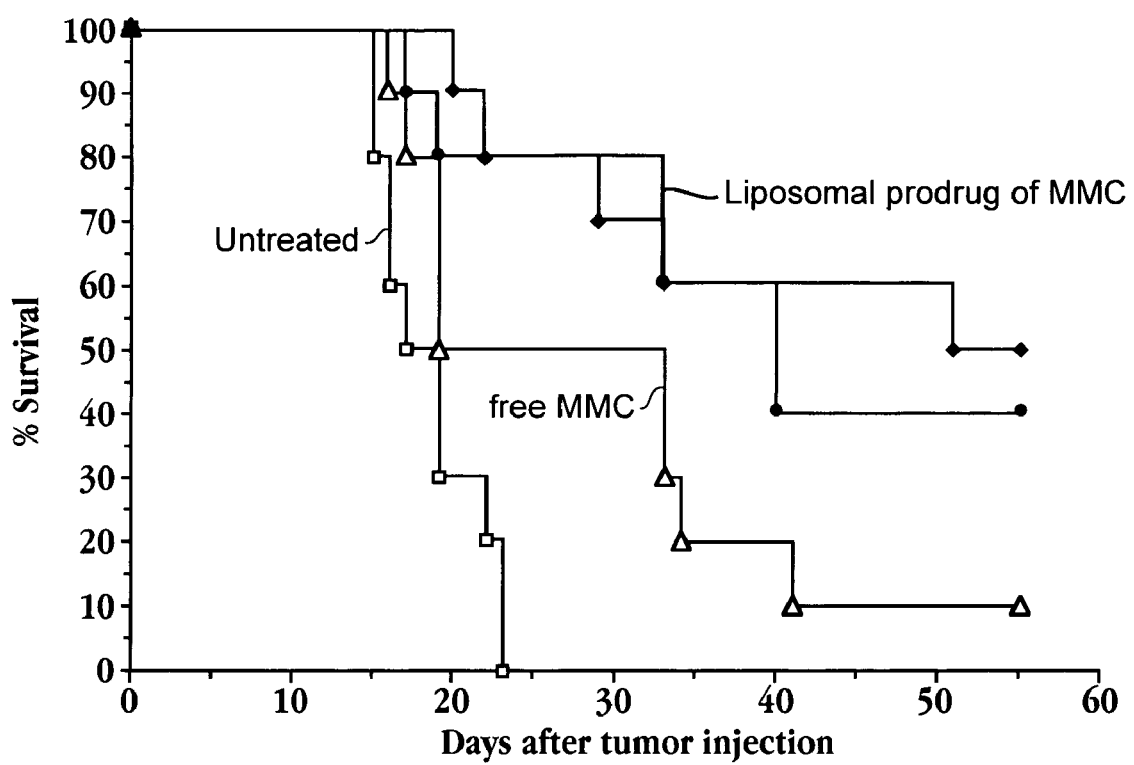
FIG. 17 is a plot of percent survival as a function of time after inoculation with C26 tumor cells in mice left untreated (squares), treated with free mitomycin C (triangles) at 6 mg/kg, or treated with liposomes comprised of HSPC/mPEG-DSPE/lipid-DTB-mitomycin C at a single dose of 6 mg/kg (circles) or two doses of 6 mg/kg and cysteine (diamonds)

In another study, mice were inoculated intraperitoneally with $10^6$ C26 tumor cells. Five days after inoculation, the mice were treated with 6 mg/kg intravenously in free form or as a drug-DTB-lipid conjugated incorporated into liposomes. The results are shown in FIG. 17, where the percent survival as a function of time after inoculation with C26 tumor cells in mice is plotted. Mice left untreated (squares) failed to survive past test day 23. At test day 40, only 10% of the mice treated with 6 mg/kg free mitomycin C (triangles) were living. In contrast, at test day 40, more than 30% of the mice treated with 6 mg/kg mitomycin C in the form of a prodrug in a liposome (circles), and more than 40% of the mice treated with 6 mg/kg (two doses) of the liposomal formulation (diamonds) were living. It is noteworthy that the mice treated with the liposomal formulation could tolerate a substantially higher dose, e.g., about 2-fold and in some cases 3-fold higher, of mitomycin C than when the drug in free form.

In another study, a subline of M109 cells selected for multi-drug resistance, M109R cells, was used. Mice were inoculated with the M109R carcinoma drug-resistant cells and then treated on days 5 and 12 intravenously with a test substance. The results are shown in FIGS. 18-19.

Figure 18:
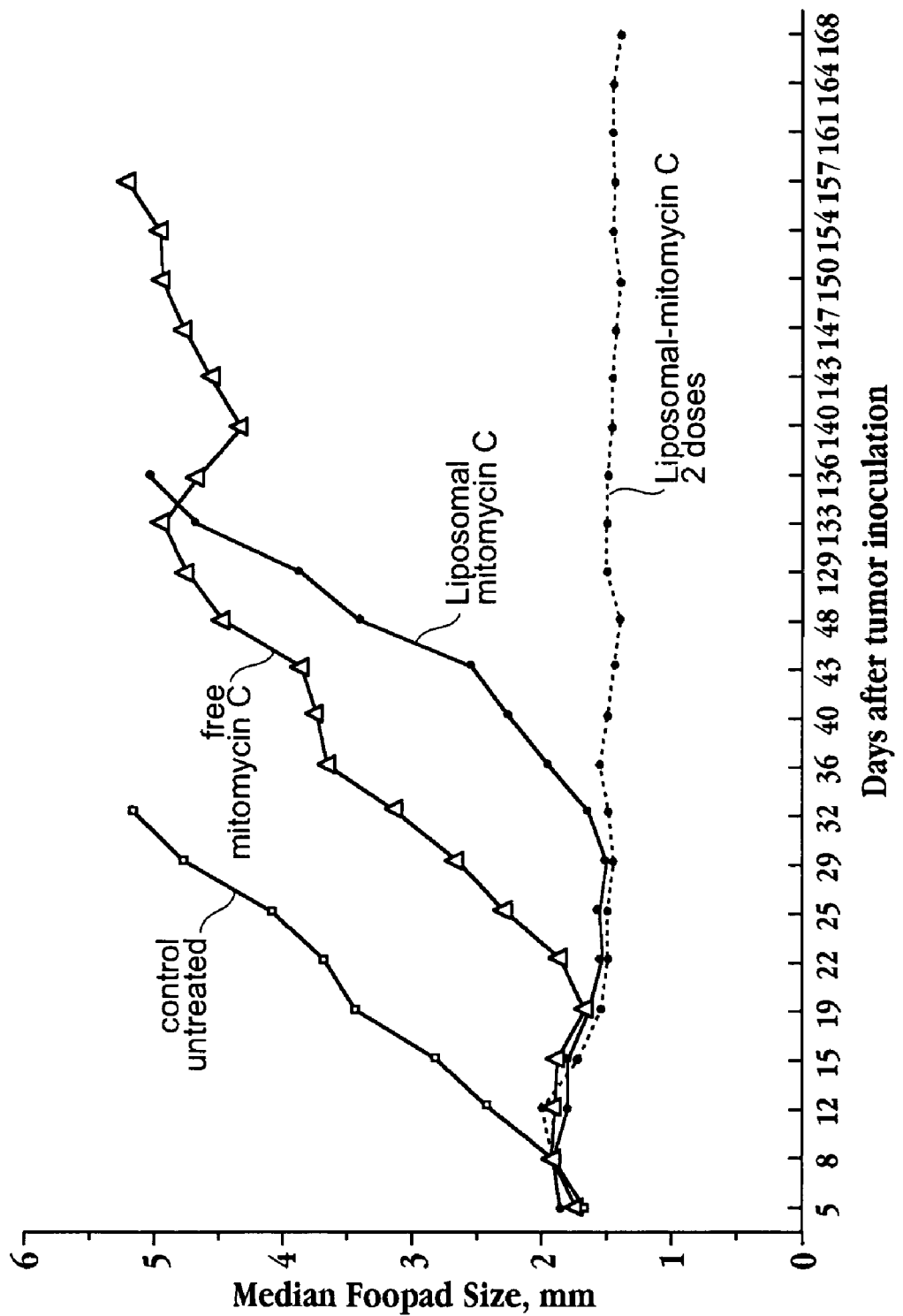
FIG. 18 is a plot of median footpad size, in mm, as a function of time after inoculation with M109-R tumor cells in mice left untreated (open squares), treated with free mitomycin C (open triangles) at 8 mg/kg, treated with one dose (closed circles, solid line) or two doses (closed circles, dashed line) of liposomes comprised of HSPC/mPEG-DSPE/lipid-DTB-mitomycin C at 8 mg/kg.

FIG. 18 shows the median footpad size, in mm, as a function of time after inoculation with M109R tumor cells. Mice left untreated (open squares) had a continual increase in tumor size. Mice treated with 8 mg/kg liposomes comprised of HSPC/mPEG-DSPE/lipid-DTB-mitomycin C (closed circles, solid line) had a smaller footpad size than mice treated with a similar dose free mitomycin C (open triangles), until about day 130. Mice treated with two 8 mg/kg doses of liposomes comprised of HSPC/mPEG-DSPE/lipid-DTB-mitomycin C (closed circles, dashed line) had little to no measurable increase in footpad size over the 168 day test period.

Figure 19A:
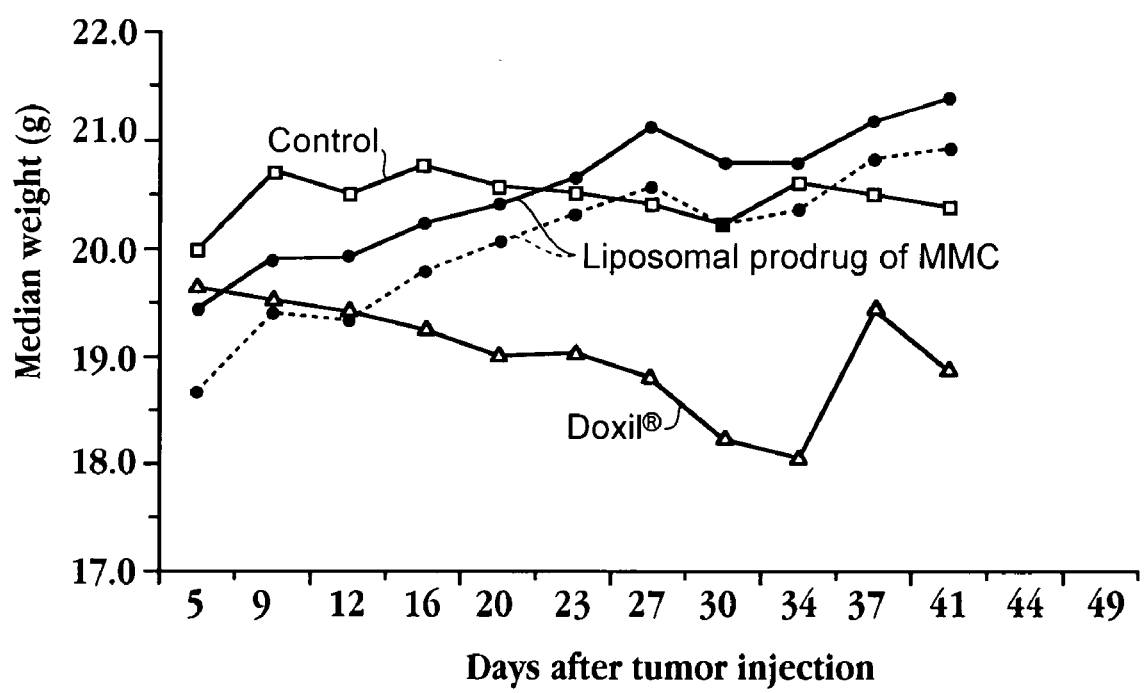
FIG. 19A is a plot of median weight, in grams, as a function of days after tumor inoculation, for mice left untreated (open squares), treated with two 10 mg/kg doses of doxorubicin entrapped in liposomes having a coating of polyethylene glycol chains (Stealth®, open triangles), treated with two doses of liposomes comprised of HSPC/mPEG-DSPE/lipid-DTB-mitomycin C at 10 mg/kg (closed circles) without cysteine (closed circles, solid line) or with 5 mg/kg cysteine (closed circles, dashed line)
Figure 19B:
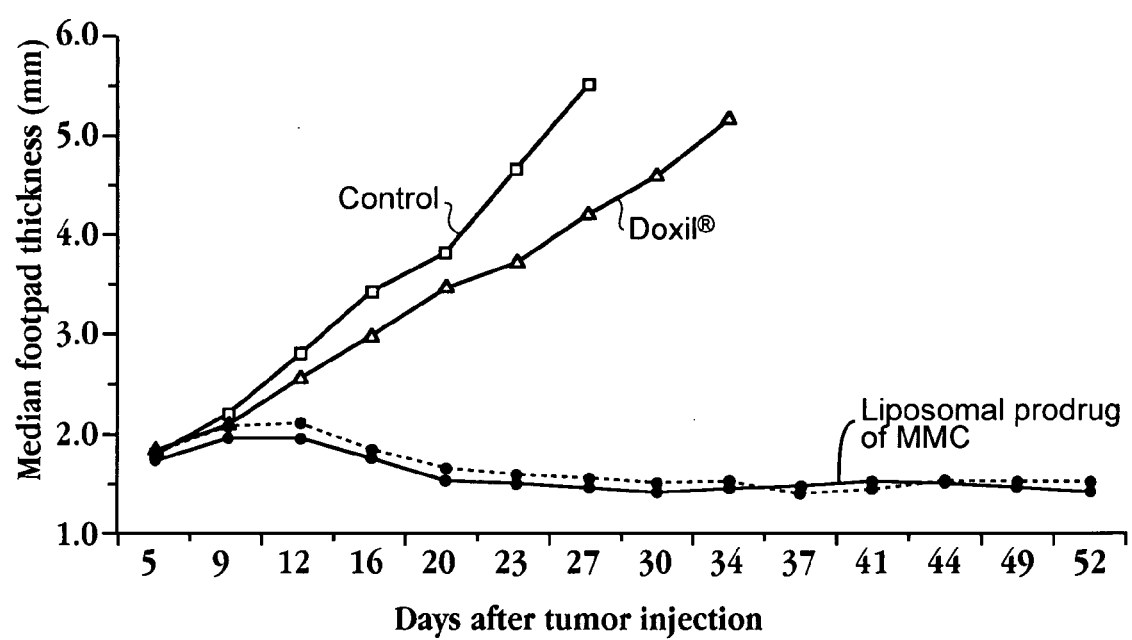
FIG. 19B is a plot of median footpad thickness, in mm, as a function of days after tumor inoculation, for mice left untreated (open squares), treated with two 10 mg/kg doses of doxorubicin entrapped in liposomes having a coating of polyethylene glycol chains (Stealth®, open triangles), treated with two doses of liposomes comprised of HSPC/mPEG-DSPE/lipid-DTB-mitomycin C at 10 mg/kg (closed circles) without cysteine (solid line) or with 5 mg/kg cysteine (dashed line)
Figure 19C:
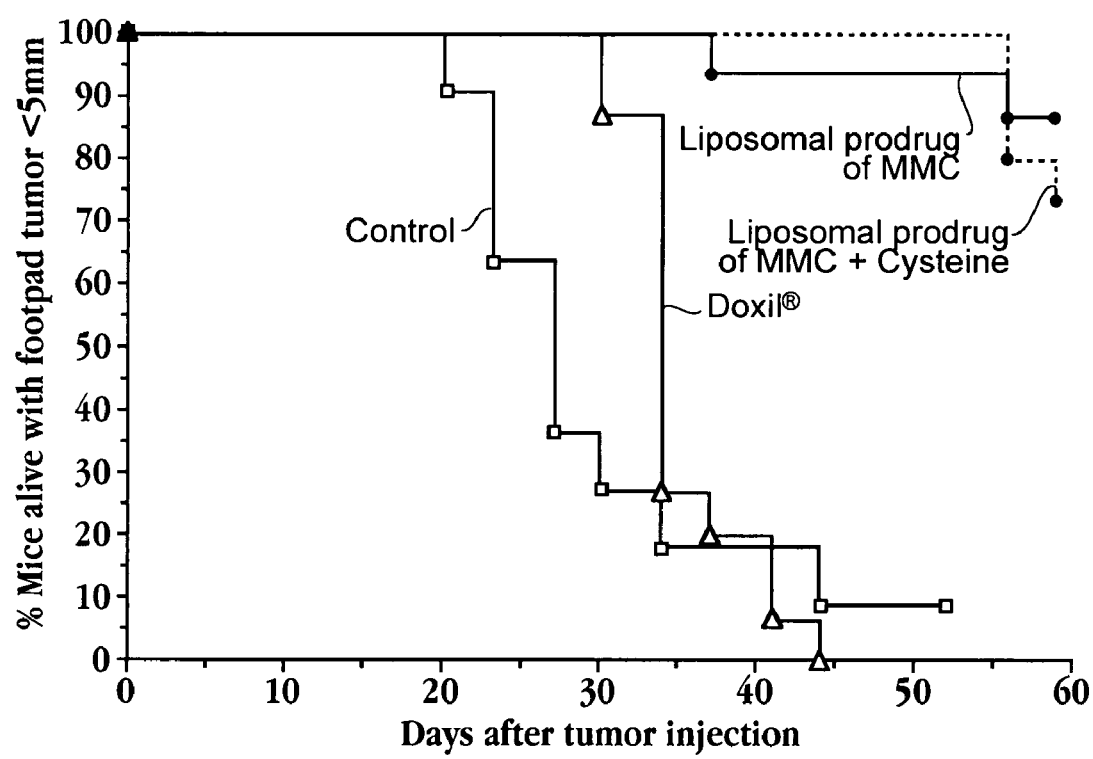
FIG. 19C is a plot of the percentage of mice alive with a footpad tumor of less than 5 mm as a function of days after tumor inoculation of M 109R cells, for mice left untreated (open squares), treated with two 10 mg/kg doses of doxorubicin entrapped in liposomes having a coating of polyethylene glycol chains (Stealth®, open triangles), treated with two doses of liposomes comprised of HSPC/mPEG-DSPE/lipid-DTB-mitomycin C at 10 mg/kg (closed circles) without cysteine (solid line) or with 5 mg/kg cysteine (dashed line).

FIGS. 19A-19B show the results of similar test mice but the mitomycin C dose was 10 mg/kg and cysteine was administered to one of the test groups. FIG. 19A shows the median weight of the test mice, in grams, as a function of days after tumor inoculation, for mice left untreated (open squares), treated with two 10 mg/kg doses of doxorubicin entrapped in liposomes having a coating of polyethylene glycol chains (Stealth®, open triangles), treated with two doses of liposomes comprised of HSPC/mPEG-DSPE/lipid-DTB-mitomycin C at 10 mg/kg (closed circles) without cysteine (closed circles solid line) or with 5 mg/mouse cysteine (closed circles, dashed line). The mice treated with liposomal-doxorubicin had a loss of weight, indicating that this was indeed the maximal tolerated dose that they could tolerate. In contrast, no weight loss was observed with liposomal MMC prodrug with or without cysteine.

FIG. 19B shows the median footpad thickness for the test animals. The mice treated with mitomycin C (two doses of 10 mg/kg on days 5 and 12) in the form of liposomes comprised of HSPC/mPEG-DSPE/lipid-DTB-mitomycin C function (closed circles) with (closed circles, dashed line) and without (closed circles, solid line) cysteine had little to no growth of footpad size. In fact, on a mouse individual basis, 11 out of 15 mice with measurable tumors had a complete tumor regression. Left untreated (open square) or treated with liposome entrapped doxorubicin (open triangles), the footpad thickness increased. The data from this study is also presented in FIG. 19C as the percentage of mice alive with a footpad thickness of less than 5 mm as a function of days after tumor inoculation.

The data shown in FIGS. 18-19 indicates that mitomycin C administered in the form of drug-lipid conjugate incorporated into liposomes is able to be taken up by multi-drug resistant cells, and accumulate in the cells to an amount sufficient for cytotoxicity. The M109R cells were unresponsive to liposome-entrapped doxorubicin (FIG. 19B), as expected for this drug-resistant carcinoma model.

From the foregoing, various aspects and features of the invention are apparent. The studies herein show that mitomycin C when formulated as a lipid-DTB-mitomycin C prodrug can be administered in vivo. This finding is significant given the fact that mitomycin C in free form is extremely toxic and, thus, often unsuitable for in vivo use. Yet, when administered to animals in the form of a lipid, prodrug conjugate, mitomycin C can be administered at 2-fold or 3-fold the dose of the drug in free form. The studies herein also show that multi-drug resistant cells are able to take up the mitomycin C when administered in the form of the lipid-DTB-drug conjugate. The research literature indicated that various primary tumors have an increased level of thioredoxin, a disulfide reducing enzyme, relative to healthy tissue (Powis et al., *Free Radical Biology & Med.*, 29:312 (2000); Engman, L., et al., Bioorganic and Medicinal Chemistry 11:5091, (2000)). The increased level of thioredoxin in tumor cells offers a unique synergy with the mitomycin C conjugate described here, since a natural source of a reducing enzyme is concentrated in the target tissue.

V. EXAMPLES

The following examples further illustrate the invention described herein and are in no way intended to limit the scope of the invention.

Materials

All materials were obtained from commercially suitable vendors, such as Aldrich Corporation.

Example 1

Synthesis of para-diacyidiglyceroldithiobenzalcohol (Compound IV) and ortho-diacyidiglyceroldithiobenzalcohol A. para-diacyldiglyceroldithiobenzalcohol This reaction is illustrated in FIG. 1. The procedure of Snyder, W. R. (*Journal of Lipid Research*, 28:949 (1987) was followed to prepare Compounds II and III.

A 100 ml round bottom flask containing 3-mercapto-1,2-propanediol (Compound I, 1 g, 9.26 mmol) in 5 ml of water was placed in an ice-bath. To this rapidly stirring flask, hydrogenperoxide (exactly 0.5 mole equivalent, 525 µl, 4.63 mmol) was dropwise added while maintaining the temperature between 30-40° C. At the end of the exothermic process, the reaction was allowed to stir overnight at room temperature. Water was azeotroped with rotary evaporation by successive addition of acetonitrile in 20 ml aliquots. The process of acetonitrile addition was repeated 3-4 times or until all water was removed, yielding a clear oil. After scratching the flask with a metal spatula and cooling overnight at −20° C., the oily product solidified (Compound II, rac-3,3'-dithiobis(1,2-propanediol)). The chalky solid was dried in vacuo over $P_2O_5$. Yield: 630 mg, 63%. $^1$HNMR ($CD_3OD$, 360 MHz) δ 2.77,2.95 (2×d, $CH_2OH$, 2H), 3.59 (M, $SCH_2$, 2H), 3.87 (m, CH, 1H) ppm.

The rac-3,3'-dithiobis(1,2-propanediol) product (Compound II) was acylated by adding the compound (980 mg, 4.6 mmol) to an oven-dried 100 mL round bottom flask and dissolving in dry methylene chloride (40 mL). To this, stearic acid (4.92 g, 17.1 mmol) and 4-dimethylamino) pyridinium 4-toluenesulfonate (1.38 g, 4.6 mmol) as the catalyst was and stirred at room temperature (25° C.) for 20 minutes. Then diisopropylcarbodiimide (3.1 mL, 20 mmmol) was pipetted and reacted overnight at room temperature. TLC silic on GF (10% ethylacetate in hexane) showed the complete reaction of the diol group. (rac-3,3'-dithiobis(1,2-propanediol) $R_f$=0.60; rac-3,3'-dithiobis(1,2-propanedistearoyl) $R_f$=0.35). Amberlyst® A-21 slightly basic ion-exchange resin (~3 g) and Amberlyst® 15 strongly acidic ion-exchange resin (~3 g) were added to the reaction mixture. After 30 minutes of shaking, the resins were filtered and the filtrate was taken to dryness. The residue was recrystallized from isopropanol three time (100 mL each). The solid product, rac-3,3'-dithiobis(1,2-propanedistearoyl) (Compound III), was collected and dried over $P_2O_5$. Yield: 70%, 4.1 g. Melting Point 54-55° C. $^1$HNMR ($CDCl_3$, 360 MHz) δ0.86, (t, $CH_3$, 6H), 1.22 (s, lipid, 56H), 1.48 (m, $CH_2CH_2(CO)O$, 4H), 2.26 (2×t, $CH_2(CO)O$, 4H), 2.87 (d, $CH_2S$, 2H), 4.03 & 4.22 (2×d, $CH_2CH$ of lipid, 2H), 4.97 (m, $CHCH_2$ of lipid)ppm.

In the next step, a solution of rac-3,3'-dithiobis(1,2-propanedistearoyl) (Compound III) (2.97 g, 2.33 mmol) was dissolved in toluene (30 mL) and placed in an ice bath. Sulfuryl chloride (1.9 mL, 23.2 mmol) was pipetted into the flask and the mixture was stirred at the cold ice bath temperature for 30 minutes. The flask was then placed at room temperature and stirred for another 30 minutes. Excess of sulfuryl chloride was removed with a rotary evaporator. A fresh (20 mL) aliquot of toluene was added to the reaction flask and placed on an ice bath. To this, a solution of 4-mercaptobenzalcohol (780 mg, 5.6 mmol) in toluene was added with a slow rate. After 5 hours of reaction time, all solvents were evaporated with rotary evaporation to dryness. Warm ethyl acetate (10 mL) was added to the reaction flask to dissolve the solid and insoluble matter was filtered. To the ethyl acetate solution, 50 mL of ether was added to precipitate, and the solid product (para-diacyl-diglycerol-dithiobenzalalcohol, Compound IV) was collected by filtration. This process was repeated twice. Yield: 75%.

To purify the product (para-diacyl-diglycerol-dithiobenzal-alcohol, Compound IV), a silica gel column (20×2.5 cm) in chloroform was prepared. The sample was dissolved in minimum amount of chloroform and was chromatographed with addition of two different mobile phases. First, 100% $CHCl_3$ (100ml) was eluted. This fraction contained the impurity dithiobenzyl alcohol. The confirmation was made by $^1$HNMR. Then, Changing the mobile phase to 15% methanol in chloroform, the pure product was collected by flash chromatography. By eluting 500 ml of $CH_3OH:CHCl_3$ (15:85) pure DGTBA (one spot by TLC) was collected. After evaporation of the solvents, the solid was lyophilized from t-BuOH and dried in vacuo over $P_2O_5$. The final purification dropped the yield to 40%, 1.4 g. $^1$HNMR: ($CDCl_3$, 360 MHz) δ 0.86 (t, $CH_3$, 6H), 1.22 (s, lipid, 56H), 1.48 (m, $CH_2CH_2(CO)O$, 4H), 2.26 (2×t, $CH_2(CO)O$, 4H), 2.87 (d, $CH_2S$, 2H), 4.03 & 4.22 (2×d, $CH_2CH$ of lipid, 2H), 4.69 (s, $CH_2$, bz, 2H), 4.97 (m, $CHCH_2$ of lipid), 7.36 & 7.56 (d, $CH_2$, aromatic, 4H) ppm.

5 mg of sample was submitted to a laboratory for elemental analysis (Midwest Micro Lab).

| Analysis | Theoretical | Measured |
| --- | --- | --- |
| Carbon | 70.93% | 70.67% |
| Hydrogen | 10.50% | 10.41% |
| Sulfur | 8.25% | 8.31% |

B. Ortho-diglyceroldithiobenzalcohol

A solution of rac-3,3'-dithiobis(1,2-propanedistearoyl) (Compound III) (200 mg, 0.156 mmol) was dissolved in toluene (30 mL) and placed in an ice bath. Sulfuryl chloride (39 μl, 0.47 mmol) was pipetted into the flask and the mixture was stirred at the cold ice bath temperature for 30 minutes. The flask was then placed at room temperature and stirred for another 30 minutes. Excess of sulfuryl chloride was removed with a rotary evaporator. A fresh (20 mL) aliquot of toluene was added to the reaction flask and placed on an ice bath. To this, a solution of 2-mercaptobenzalcohol (48 mg, 35 mmol) in toluene was added with a slow rate. After 5 hours of reaction time, all solvents were evaporated with rotary evaporation to dryness. Warm ethyl acetate (10 mL) was added to the reaction flask to dissolve the solid and insoluble matter was filtered. To the ethyl acetate solution, 50 mL of ether was added to precipitate, and the solid product (ortho-diacyl-diglycerol-dithiobenzalalcohol) was collected by filtration. This process was repeated twice. The solid was dried in vacuo over $P_2O_5$. Yield: 75%, 190 mg. $^1$HNMR: ($CDCl_3$, 360 MHz) δ 0.86 (t, $CH_3$, 6H), 1.25 (s, lipid, 56H), 1.58 (m, $CH_2CH_2(CO)O$, 4H), 2.28 (2×t, $CH_2(CO)O$, 4H), 2.91 (d, CH2S, 2H), 4.14 & 4.35 (2×d, $CH_2CH$ of lipid, 2H), 4.86 (s, CH2, bz, 2H), 5.26 (m, $CHCH_2$ of lipid), 7.31 (m, aromatic, 2H), 7.48 & 7.75 (d, aromatic, 2H) ppm.

Example 2

Synthesis of para-diacyldiglyceroldithiobenzal-mitomycin C (Compound XVIII)

This reaction is illustrated in FIG. 3A.

A 50 mL round bottom flask was charged with phosgene (3.1 mmol) and toluene (5 mL) and the solution was cooled to 0° C. A solution of para-diacyl-diglycerol-dithiobenzal-alcohol, (Compound IV, prepared as described in Example 1, 0.31 mmol) in toluene (2.5 mL) was prepared. The alcohol solution was then added dropwise to the phosgene solution. The mixture was allowed to warm to room temperature overnight. After 18 hours, the solution was concentrated in vacuo to remove excess phosgene. The crude acyl chloride was redissolved in toluene (5 mL).

A solution of mitomycin C (0.31 mmol), dimethylaminopyridine (0.031 mmol) and DMF (1 mL) was prepared. The mitomycin C solution was added drop-wise the acyl chloride solution. After 1 hour, the toluene was evaporated off and the crude product was chromatographed (1:1 hexane: ethyl acetate) on silica. The purified product was then taken up in t-BuOH (50 mL) and lyophilized. The product was a purple solid (183 mg, 53%). $R_f$=0.38 (50% hexane: ethyl acetate); $^1$H NMR (360 MHz, CDCl$_3$) δ 0.88 (t, J=6.8 Hz, 6H), 1.26 (s, 58 H), 1.58-1.63 (m, 4H), 1.76 (s, 3H), 2.29 (t, J=7.6 Hz, 4H), 2.93-2.96(m, 2H), 3.19 (s, 3H), 3.29 (dd, J=4.7 and 2.9 Hz, 1H), 3.41 (dd, J=5.0 and 2.2 Hz, 1H), 3.48 (dd, J=13.7 and 2.5 Hz, 1H), 3.67 (dd, J=11.5 and 4.7 Hz, 1H), (ddd, J=12.2 and 5.8 and 2.5 Hz, 1H), 4.27-4.36 (m, 2H), 4.43 (d, J=13.3 Hz, 1H), 4.61 (s, 2H), 4.90 (ddd, J=10.4 and 5.0 and 2.2 Hz, 1H), 5.00-5.12 (m, 3H), 5.26-5.30 (m, 1H), 7.32 (d, J=8.6 Hz, 2H), 7.50 (d, J=7.9 Hz, 2H); MALDI MS calcd for $C_{62}H_{99}N_4O_{11}S_2Na$: 1164, found m/z 1164 (M+Na).

Example 4

Liposome Preparation

A. Liposomes Containing Cholesterol

1. Liposome Preparation 59 mg HSPC, 14.4 mg cholesterol, 17.4 mg mPEG-DSPE, and 7.4 mg para-distearoyl-DTB-mitomycin C (molar ratio of 60/30/5/5) were added to 1 mL dehydrated ethanol at 60-65° C. and mixed until dissolved, approximately 10 minutes.

A hydration medium composed of 10 mM histidine and 150 mM NaCl in distilled water was warmed to 70° C.

The warm lipid solution was rapidly added to the warm (63-67° C.) hydration medium, with mixing, to form a suspension of liposomes having heterogeneous sizes. The suspension was mixed for one hour at 63-67° C.

2. Extrusion

The liposomes were sized to the desired mean particle diameter by controlled extrusion through polycarbonate filter cartridges housed in Teflon-lined stainless steel vessels. The liposome suspension was maintained at 63-65° C. throughout the extrusion process, a period of 6-8 hours.

3. Diafiltration

Ethanol was removed from the liposome suspension by diafiltration. A histidine/sodium chloride solution was prepared by dissolving histidine (10 mM) and sodium chloride (150 mM) in sterile water. The pH of the solution was adjusted to approximately 7. The solution was filtered through a 0.22 μm Durapore filter. The liposome suspension was diluted in approximately a 1:1 (v/v) ratio with the histidine/sodium chloride solution and diafiltered through a polysulfone hollow-fiber ultrafilter. Eight volume exchanges were performed against the histidine/sodium chloride solution to remove the ethanol. The process fluid temperature was maintained at about 20-30° C. Total diafiltration time was approximately 4.5 hours.

4. Sterile Filtration

The liposome suspension was heated to 33-38° C. and filtered through a 0.2 μm Gelman Supor polyethersulfone filter. Total filtration time was approximately 10 minutes.

After each processing step (hydration, extrusion, dialysis and filtration) the lipid concentration and conjugate/drug concentration were determined by HPLC. Liposome particle size was measured by dynamic light scattering and the amount of "free", unbound mitomycin C in the external suspension medium was measured by HPLC.

|  | lipid-DTB-MMC[1,2] Conjugate (μg/mL) | lipid (mg/mL) | conjugate/ lipid ratio | Liposome Size (nm) 90° | Liposome Size (nm) 30° | free MMC[2] (%) |
|---|---|---|---|---|---|---|
| post-hydration | 699 | 12.50 | 56 | — | — | 2 |
| post-extrusion | 369 | 8.49 | 43 | 105 | 186 | 4 |
| post-dialysis | 311 | 7.78 | 40 | — | — | 0 |
| post-filtration | 315 | 7.22 | 44 | 103 | 120 | 0 |

[1]Conjugate = Compound XVIII, para-distearoyl-DTB-mitomycin C
[2]MMC = mitomycin C

B. Cholesterol-Free Liposome Formulation

Liposomes were prepared as described above with a lipid composition of HSPC, mPEG-DSPE and para-distearoyl-DTB-mitomycin C in a molar ratio of 90/5/5. Specifically, 88.5 mg HPSC, 17.9 mg mPEG-DSPE (PEG MW 2000 Daltons) and 7.3 mg of the conjugate were dissolved in 1 mL ethanol. Liposome size, lipid and drug concentration and free mitomycin C concentration in the external suspension medium were determined after each processing step.

|  | lipid-DTB-MMC[1,2] Conjugate (μg/mL) | lipid (mg/mL) | conjugate/ lipid ratio | Liposome Size (nm) 90° | Liposome Size (nm) 30° | free MMC[2] (%) |
|---|---|---|---|---|---|---|
| post-hydration | 525 | 10.94 | 48 | — | — | 3 |
| post-extrusion | 466 | 9.95 | 47 | 85 | 110 | 6 |
| post-dialysis | 404 | 8.35 | 48 | — | — | 0 |
| post-filtration | 378 | 7.92 | 48 | 82 | 93 | 0 |

[1]Conjugate = Compound XVIII, para-distearoyl-DTB-mitomycin C
[2]MMC = mitomycin C

Example 5

HPLC Conditions for in vitro Characterization

Liposomes prepared as described in Examples 4A-4B were diluted in 0.6 M octaylglucopyranoside. The liposomes were incubated in the presence of 150 mM cysteine at 37° C. Samples with withdrawn at time zero, 30 minutes, 1 hour, 2 hours, 4 hours and 24 hours. A 20 μL volume was analyzed by HPLC using a Water Symmetry C8 3.5×5 cm column. The flow rate was 1 mL/min and the mobile phase gradient as follows:

| start | 10% | MEOH | 90% 10 mM NaPO$_4$, pH = 7 |
|---|---|---|---|
| 5 min. | 25% | MeOH | 75% 10 mM NaPO$_4$, pH = 7 |
| 10 min. | 25% | MEOH | 75% 10 mM NaPO$_4$, pH = 7 |
| 15 min. | 100% | MeOH | — |
| 25 min. | 100% | MeOH | — |
| 30 min. | 10% |  | 90% 10 mM NaPO$_4$, pH = 7 |
| 35 min. | 10% | MEOH | 90% 10 mM NaPO$_4$, pH = 7 |

Example 6

Cytotoxicity Studies

A. Liposome Preparation

Liposomes, prepared as described in Example 4A-4B, were composed of HSPC/mPEG-DSPE/distearoyl-DTB-mitomycin C (90/5/5) or HSPC/cholesterol/mPEG-DSPE/distearoyl-DTB-mitomycin C (90/45/5/5). The liposome preparations were sterile filtered through 0.45 μm cellulose membranes and were not downsized via extrusion. After liposome formation, mitomycin C concentration was determined by absorbance at 360 nm in liposomes solubilized by 10-20 fold dilution in isopropanol and the phospholipid concentration was determined by inorganic phosphate assay.

The liposomes containing cholesterol had an average diameter of 275±90 nm. The cholesterol-free liposomes had an average diameter of 150±50 nm. The phospholipid concentration in both liposome formulations was 10 μM/mL and the concentration of mitomycin C in both formulations was 120 μg/mL.

B. Chemosensitivity Assay and Growth Rate Determination

The cytotoxic effect of free mitomycin C or mitomycin C in the form of a distearoyl-DTB-mitomycin C conjugate incorporated into liposomes was assayed colorimetrically by a methylene blue staining method described previously (Horowitz, A. T. et al., *Biochim. Biophys. Acta*, 1109:203-209 (1992)) with slight modifications. Upon completion of the assay, the cells were fixed and evaluated using the methylene blue staining assay.

In the assay, 1500 M109 mouse carcinoma cells from exponentially growing cultures in 200 μL aliquots (RPMI-1640 medium+10% fetal bovine serum) were plated onto 96 well flat-bottom microtiter plates. Following 20 hours in culture, during which cells attached and resumed growth, 20 μL of the test formulations (free mitomycin C or liposome formulations) was added to each well. For each 10-fold increase in drug concentration, four drug concentration points were tested. Each test was performed in triplicate wells and in two parallel plates. The cells were treated continuously for 72 hours.

After the 72 hour treatment period, the cultures were fixed by the addition of 50 μl 2.5% glutaraldehyde to each well for 10 minutes. The plates were washed three times with deionized water, once with 0.1 M borate buffer (pH 8.5) and then stained for 60 minutes with 100 μl methylene blue (1% in 0.1 M buffer borate, pH 8.5) at room temperature (20-25° C.). The plates were rinsed in five baths of deionized water to remove non-cell bound dye and then dried. The dye was extracted with 200 μL 0.1 N HCl for 60 minutes at 37° C. and the optical density was determined using a microplate spectrophotometer.

The cell number determined by counting cells with a hemocytometer correlated well with the spectrophotometric absorbance. The initial cell plating density was chosen to ensure a linear relationship between cell number and absorbance at the end of the study. In each study, six wells were fixed before drug was added to determine the initial average absorbance. This value was used to calculate growth rate (GR) and doubling times (DT) of control and drug-treated cells using the following equation: $DT = \ln 2 / \ln[(OD_t/OD_c)/h]$; where DT = doubling time in hours; $OD_t$ = optical density of test well at the end of the study; $OD_c$ = optical density of control well at the start of the study; h = duration of incubation in hours.

The growth rate was calculated as $GR = (\ln 2/DT)$. The percent growth inhibition or percent of control growth rate was obtained by dividing the growth rate of drug-treated cells by the growth rate of the untreated, control cells. The drug concentration which caused a 50% inhibition of the control growth rate ($IC_{50}$) was calculated by interpolation of the two closest values of the growth inhibition curve.

Mitomycin C was assayed in the range $10^{-8}$-$10^{-5}$ M. The liposomal formulations with conjugate-bound were assayed in the range $10^{-8}$-$3 \times 10^{-5}$ M. For interaction studies cysteine (SIGMA, St. Louis, Mo.) was added together with the mitomycin C or liposome formulations to final concentration of 150, 500, or 1000 μM.

The results are shown in Table 1 and in FIGS. 10, 11A-11B and 12.

Example 7

In vivo Pharmacokinetic Study

A. Liposome Formulations

Liposomes containing cholesterol and cholesterol-free liposomes were prepared as described in Example 5A and 5B.

A solution of mitomycin C in free form was prepared by dissolving 11.9 mg of mitomycin C in 119 μL ethanol. After dissolution, approximately 11.8 μL of a solution of 10 mM histidine/150 mM saline was added. Prior to use, the mitomycn C solution was diluted to 100 μg/mL with the histidine/saline solution and filtered.

B. Animals

Eight rats were randomized into treatment groups as follows:

| Rat No. | Weight (mg) | Formulation | MMC Conc. (mg/mL) | Dose (mL) | Dose (mg/kg) |
|---|---|---|---|---|---|
| 1 | 262.9 | liposomes with chol. | 0.088 | 1.5 | 0.50 |
| 2 | 268.2 | liposomes with chol. | 0.088 | 1.5 | 0.49 |
| 3 | 264.0 | chol-free liposomes | 0.106 | 1.5 | 0.53 |
| 4 | 238.1 | chol-free liposomes | 0.106 | 1.5 | 0.67 |
| 5 | 226.0 | free MMC | 0.1 | 2.26 | 0.66 |
| 6 | 232.0 | free MMC | 0.1 | 2.32 | 0.88 |
| 7 | 250.0 | free MMC | 0.1 | 2.60 | 0.80 |
| 8 | 263.0 | free MMC | 0.1 | 2.63 | 0.59 |

A single intravenous injection of the test formulation was administered as a bolus dose. Blood samples were taken from each animal at the following times after injection: 30 seconds, 15 minutes, 30 minutes, 1 hour, 2 hours, 4 hours, 8 hours, 24 hours, 48 hours, 72 hours and 96 hours. The quantity of mitomycin C in the blood samples was determined by the HPLC procedure given below. A 200 mM iodoacetamine solution was prepared by placing 199.3 mg of iodoacetamide in 5.1 mL of 7.5% DTA. 15 μL of the 200 mM iodoacetamide solution was placed in each 1 μL of blood sample.

C. HPLC Method for Measuring Mitomycin C in Plasma

1. Solution Preparation

An aqueous buffer containing 10 mM ammonium phosphate, pH=7 was prepared by placing 1.321 g of ammonium phosphate into a 1 L volumetric flask filled with deionized water. The mixture was stirred and the pH was adjusted to 7.0 with o-phosphoric acid. The buffer was filtered through a 0.45 μm nylon filter before use.

A mobile phase of methanol and the aqueous buffer were mixed via a gradient program using a Waters Alliance binary pump.

2. Preparation of Standard Solution and Quality Control Samples

Two separate weights of mitomycin C and mitomycin C conjugate were prepared as standards and quality control samples. One mg of mitomycin C and of mitomycin C conjugate were weighed and dissolved in 1 mL diluent (20% chloroform and 80% methanol mixture) separately. The concentration of the stock solution for both compounds was 1 mg/mL. Several dilutions were made in diluent to obtain concentrations from 5 μg/mL to 100 μg/mL for standard and quality control samples.

An aliquot of 0.1 mL rat plasma was spiked with appropriate volumes (10 μL-50 μL) of mitomycin C and mitomycin C conjugate standard solutions. The concentration ranges were 0.05-5.0 μg/mL and 0.1-5 μg/mL for mitomycin C and mitomycin C conjugate, respectively. The final volume was adjusted to 1 mL with methanol. A similar procedure was followed to prepare quality control samples. The concentrations of quality control samples was 0.1, 0.5 and 5 μg/mL for mitomycin C and 0.1, 1 and 5 μg/mL for mitomycin C conjugate in rat plasma. The samples were spun down at 3,000 rpm for 10 minutes at room temperature. 300 μL of supernatant was transferred to HPLC vials containing 300 μL insert for injection.

3. Sample Preparation

100 μL of plasma sample was denatured with 900 μL of methanol followed by centrifugation for 10 minutes at 3,000 rpm. An aliquot of 300 μL supernatant was transferred to an HPLC vial containing a 300 μL insert for injection.

4. Chromatographic Conditions

A Supelco® C-8, 5 μ, 4.6 mm×5 cm column was used. The mobile phase A was 10 mM ammonium phosphate, pH 7. Mobil phase B was methanol. The flow rate was 1 mL/min and detection was by UV at 360 nm. The injection volume was 40 μL and the typical run time was 15 minutes. The gradient program was as follows:

| Time (minutes) | Amount of Mobil Phase A (%) | Amount of Mobil PhaseB (%) |
|---|---|---|
| 0 | 90 | 10 |
| 4 | 70 | 30 |
| 8 | 0 | 100 |
| 12 | 90 | 10 |
| 15 | 90 | 10 |

5. Assay and Calculations

The prepared linearity standards (six concentration levels) from low to high concentration were injected. The quality control and plasma samples were then injected for analysis.

Peak area and retention times were determined by the PE-Nelson Turbochrom (Version 4.1) system. Concentrations of mitomycin C and mitomycin C conjugate were calculated using a linear regression program. The linearity of the method was evaluated suing standard responses from six concentration levels. The data were fit to the linear regression equation y=B*x+A with a weighting factor of $1/x^2$. The precision and accuracy of the method were evaluated from the back-calculated concentrations of the standards as well as from the quality control samples.

The results are shown in FIGS. 13A-13B.

Example 8

In Vivo Studies

Female 10-week-old BALB/c mice were maintained in a specific pathogen-free facility. M109 cells or M109R cells were grown in in vitro suspension. The mice were injected into the right hind footpad with 50 μL ($10^6$ cells). The footpad thickness was measured with calipers until completion of the study, when the mice were sacrificed, the final number of tumors recorded, and the control and tumor-inoculated footpads were sectioned at the ankle level and weighed. Tumor weight was estimated as the difference between the weight of the normal and tumor-bearing footpad. The statistical significance of differences in the final incidence of tumors per group was analyzed by contingency tables and the Fisher's exact test. The results are shown in FIGS. 15A-15B and FIGS. 16A-16B, FIG. 18, FIG. 19A-19C.

Although the invention has been described with respect to particular embodiments, it will be apparent to those skilled in the art that various changes and modifications can be made without departing from the invention.

It is claimed:

1. A method for administering mitomycin C to a multi-drug resistant cell,
   comprising
   providing mitomycin C in the form of a liposome composition comprised of a vesicle-forming lipid and of between about 1 to about 30 mole percent of a conjugate having the general form:

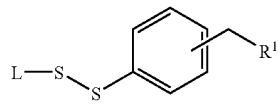

wherein L is a hydrophobic moiety suitable for incorporation into a liposomal lipid bilayer, $R^1$ is mitomycin C covalently attached to the dithiobenzyl moiety, and where orientation of the $CH_2R^1$ group is selected from the ortho position and the para position.

2. The method of claim 1, wherein said providing includes providing mitomycin C covalently attached by a urethane linkage.

3. The method of claim 1, wherein said providing includes providing a conjugate wherein L is selected from the group consisting of cholesterol, a diacylglycerol, and a phospholipid.

4. The method of claim 1, wherein said providing includes providing a conjugate comprising mitomycin C covalently linked to the dithiobenzyl moiety to form a conjugate having the structure:

[Structure: L—S—S—C6H4—CH2—O—C(=O)—R4]

wherein R⁴ represents a residue of mitomycin C.

5. The method of claim 4, wherein a secondary amine moiety of R⁴ forms a urethane linkage between the dithiobenzyl and mitomycin C.

6. A method for reducing the in vivo cytotoxicity of mitomycin C, comprising
providing mitomycin C in the form of a liposome composition comprised of a vesicle-forming lipid and of between about 1 to about 30 mole percent of a conjugate having the general form:

[Structure: L—S—S—C6H4—R1]

wherein L is a hydrophobic moiety suitable for incorporation into a liposomal lipid bilayer, R¹ is mitomycin C covalently attached to the dithiobenzyl moiety, and where orientation of the CH₂R¹ group is selected from the ortho position and the para position.

7. The method of claim 6, wherein said providing includes providing mitomycin C covalently attached by a urethane linkage.

8. The method of claim 6, wherein said providing includes providing a conjugate wherein L is selected from the group consisting of cholesterol, a diacylglycerol, and a phospholipid.

9. The method of claim 6, wherein said providing includes providing a conjugate comprising mitomycin C covalently linked to the dithiobenzyl moiety to form a conjugate having the structure:

[Structure: L—S—S—C6H4—CH2—O—C(=O)—R4]

wherein R⁴ represents a residue of mitomycin C.

10. The method of claim 9, wherein a secondary amine moiety of R⁴ forms a urethane linkage between the dithiobenzyl and mitomycin C.

* * * * *